United States Patent [19]

Ooura et al.

[11] Patent Number: 5,681,995
[45] Date of Patent: Oct. 28, 1997

[54] ULTRASONIC FLAW DETECTING APPARATUS FOR INSPECTING MULTI-LAYER STRUCTURE AND METHOD THEREOF

[75] Inventors: Takehiro Ooura; Kazunori Koga, both of Hitachi; Fuminobu Takahashi, Hitachinaka; Norio Awamura, Takehara, all of Japan

[73] Assignees: Hitachi, Ltd.; Babcock-Hitachi Kabushiki Kaisha, both of Tokyo, Japan

[21] Appl. No.: 614,184

[22] Filed: Mar. 12, 1996

[30] Foreign Application Priority Data

Mar. 17, 1995 [JP] Japan ................................ 7-058524

[51] Int. Cl.⁶ ........................ G01N 29/06; G01N 29/10
[52] U.S. Cl. ................... 73/622; 73/628; 73/623; 376/249; 376/252
[58] Field of Search .................... 73/597, 598, 599, 73/600, 602, 609, 614, 620, 622, 627, 628, 630, 623; 376/245, 249, 252, 291, 292

[56] References Cited

U.S. PATENT DOCUMENTS 5,118,464 6/1992 Richardson et al. .................. 376/252
5,377,237 12/1994 Richardson et al. .................. 376/252
5,492,012 2/1996 Terhune ............................ 73/598

*Primary Examiner*—Hezron E. Williams
*Assistant Examiner*—Rose M. Miller
*Attorney, Agent, or Firm*—Antonelli, Terry, Stout & Kraus, LLP.

[57] ABSTRACT

An ultrasonic flaw detecting apparatus for efficiently detecting a flaw existing in a deep portion of a multi-layer structure includes a first sensor arranged so as to transmit an ultrasonic wave into a different property layer surrounded by a medium having a different acoustic impedance in the multi-layer structure, a function generator for generating a pulse-shaped sine wave, a power amplifier for amplifying and supplying the pulse-shaped sine wave to the first sensor, a second sensor arranged so as to receive a boundary echo from the different property layer, a first amplifier for amplifying the boundary echo received by the second sensor, an intensity detector for judging the intensity of an amplified signal of the boundary echo, a third sensor arranged so as to receive an echo from a flaw inside a layer in a deep portion of the different property layer, a second amplifier for amplifying the flaw echo received by the third sensor, a recorder for recording the amplified flaw echo signal, and a control unit for reading data from the intensity detector and outputting commands to the function generator and the recorder.

10 Claims, 24 Drawing Sheets

ULTRASONIC FLAW DETECTING APPARATUS FOR INSPECTING MULTI-LAYER STRUCTURE AND METHOD THEREOF

BACKGROUND OF THE INVENTION

The present invention relates to the field of ultrasonic transmission and receiving technology, involving a method and an apparatus for inspecting a multi-layer structure utilizing ultrasonic waves and, more particularly, the invention relates to inspection technology for detecting a flaw, such as a flaw existing at a place beyond a layer surrounded by a medium having a largely different acoustic impedance, that is, a layer, for example, in the form of a gap across which an ultrasonic wave hardly transmits. The present invention relates to ultrasonic flaw detecting technology suitable for detecting a flaw existing at a place beyond a gap by selecting a most suitable ultrasonic wave frequency capable of transmitting across the gap.

In a conventional inspection apparatus for inspecting steel utilizing ultrasonic waves, a sensor which oscillates to generate ultrasonic waves transmits the ultrasonic waves into an object to be inspected directly or through a probe shoe for launching ultrasonic waves at an arbitrary incident angle.

However, when an ultrasonic wave propagates in a media having different material properties, the ultrasonic wave is reflected at the boundary surface between the different materials. Especially, when the material properties are largely different, for example, as provided by a boundary surface between steel and air, almost all of the ultrasonic wave is reflected at the boundary surface. That is, the ultrasonic wave once launched into the steel is trapped inside the steel and will hardly exit from the steel.

In case of the existence of a layer which hardly transmits an ultrasonic wave, such as a gap, the intensity of the ultrasonic wave arriving at a flaw is weak, because the transmission coefficient of the gap for an ultrasonic wave is very small. Therefore, a conventional ultrasonic inspection apparatus cannot detect a flaw existing at a place beyond a gap.

An inspection apparatus for detecting a flaw existing at a place beyond a layer which hardly transmits an ultrasonic wave, such as a gap, is disclosed in Japanese Patent Application Laid-Open No. 4-344458 (1992) or Japanese Patent Application Laid-Open No. 6-201658 (1994). The inspection apparatus uses a pulse wave containing a special frequency spectrum for detecting such a flaw.

An outline of a portion of this apparatus and the arrangement of a sensor will be described below referring to FIG. 3 and FIG. 4.

In FIG. 4, an inert gas, such as helium, is filled in a gap G and a pulse wave shown in FIG. 5 is transmitted from a sensor 40.

The transmitted ultrasonic wave passes through the gap G and then the ultrasonic wave reflected by a flaw 23 passes the gap again and is received by the sensor 40.

There is a condition under which the ultrasonic wave will pass through the gap G. Only a frequency component of the ultrasonic wave satisfying the condition can pass through the gap.

FIG. 6 is the spectrum distribution of the pulse wave shown in FIG. 5.

Only a special frequency component of the ultrasonic wave 140 in the spectrum of FIG. 6 can pass through the gap G and reach the flaw 23.

Presence or absence of a flaw can be detected by the ultrasonic wave 140 having the special frequency component which can arrive at the flaw 23.

In the prior art described above, when the spacing of the layer, such as by a gap, across which it is difficult for an ultrasonic wave to propagate, is unknown, there is a problem in that it is difficult to determine whether the ultrasonic wave has passed through the gap or not.

Further, when the spacing of the gap is not uniform, the frequency of the ultrasonic wave which is capable of arriving at the flaw after passing through the gap is different depending on the inspecting position, and therefore, there is a problem that the energy of the ultrasonic wave cannot effectively pass through the gap.

SUMMARY OF THE INVENTION

An object of the present invention is, in regard to an ultrasonic wave used for inspection of a flaw in a multi-layer structure having a middle layer, such as a gap, to provide a method and an apparatus in which the energy of the ultrasonic wave is efficiently transmitted to and received from a deep portion beyond the middle layer.

A first aspect of the present invention involves an ultrasonic flaw detecting apparatus for inspecting a multi-layer structure, which apparatus comprises an ultrasonic wave transmitting means acoustically connected to a multi-layer structure composed of not less than three layers, including a middle layer, the middle layer being formed of a medium having an acoustic impedance different from the adjacent layers on either side thereof; an ultrasonic wave receiving means acoustically connected to the multi-layer structure at a position for receiving a boundary echo from an interface of a first layer adjacent to the middle layer, the first layer existing on the transmitting means side of the middle layer; an ultrasonic wave receiving means acoustically connected to the multi-layer structure at a position for receiving an echo from the inside of a second layer existing on the other side of the middle layer from the transmitting means; a function generator for outputting a pulse-shaped sine wave applied to the transmitting means; a frequency control means for varying the sine wave frequency of the pulse-shaped sine wave output from the function generator; intensity detecting means for detecting the intensity of a signal based on an output of the ultrasonic wave receiving means for receiving a boundary echo; and a means for either recording or displaying the intensity of a signal based on an output of the ultrasonic wave receiving means for receiving the echo from the inside of the second layer.

A second aspect of the present invention involves an ultrasonic flaw detecting apparatus for inspecting a multi-layer structure, which apparatus comprises a first sensor arranged so as to transmit an ultrasonic wave in a slanting direction with respect to a multi-layer structure composed of not less than three layers, including a middle layer, the middle layer being formed of a medium having an acoustic impedance different from the adjacent layers on either side thereof; a function generator for outputting a pulse-shaped sine wave applied to the first sensor; a power amplifier for amplifying the output of the function generator; a frequency control means for varying the sine wave frequency of the pulse-shaped sine wave output from the function generator; a second sensor arranged so as to receive a boundary echo from an interface of a first layer adjacent to the middle layer, the first layer existing on the first sensor side of the middle layer; a first amplifier for amplifying a signal of the boundary echo received by the second sensor; an intensity detecting means for detecting the intensity of a signal based on an output of the first amplifier; a third sensor arranged so as to receive an echo from the inside of a second layer existing on the other side of the middle layer from the first sensor; a second amplifier for amplifying a signal of an echo received by the third sensor; and a means for recording or displaying a signal based on an output of the second amplifier.

A third aspect of the present invention involves an ultrasonic flaw detecting apparatus for inspecting a multi-layer structure, which apparatus comprises a first sensor arranged so as to transmit an ultrasonic wave in a slanting direction with respect to a multi-layer structure composed of not less than three layers, including a middle layer, the middle layer being formed of a medium having an acoustic impedance different from the adjacent layers on either side thereof, and to receive an echo from the inside of a second layer existing on the other side of the middle layer from the transmitting side; a function generator for outputting a pulse-shaped sine wave applied to the first sensor; a power amplifier for amplifying the output of the function generator; a frequency control means for varying the sine wave frequency of the pulse-shaped sine wave output from the function generator; a second amplifier for amplifying a signal of an echo received by the first sensor; a switching means for selectively connecting the power amplifier and the second amplifier to the first sensor; a second sensor arranged so as to receive a boundary echo of an interface of a first layer adjacent to the middle layer, the first layer existing on the first sensor side of the middle layer; a first amplifier for amplifying a signal of the boundary echo received by the second sensor; an intensity detecting means for detecting the intensity of a signal based on an output of the first amplifier; and a means for recording or displaying a signal based on an output of the second amplifier.

A fourth aspect of the present invention involves an ultrasonic flaw detecting apparatus for inspecting a multi-layer structure, which apparatus comprises a first sensor arranged so as to transmit an ultrasonic wave to a multi-layer structure composed of not less than three layers, including a middle layer, in a thickness direction normal to the multi-layer structure, the middle layer being formed of a medium having an acoustic impedance different from the adjacent layers on either side thereof, and to receive an echo from the inside of a second layer existing on the other side of the middle layer from the transmitting side; a function generator for outputting a pulse-shaped sine wave applied to the first sensor; a power amplifier for amplifying the output of the function generator; a frequency control means for varying the sine wave frequency of the pulse-shaped sine wave output from the function generator; a first amplifier for amplifying a signal of a boundary echo received by the first sensor; an intensity detecting means for detecting the intensity of a signal based on an output of the first amplifier; a second amplifier for amplifying a signal of an echo other than the boundary echo received by the first sensor; a switching means for switching connection of the power amplifier and the first amplifier and the second amplifier to the first sensor; and a means for recording or displaying a signal based on an output of the second amplifier.

A fifth aspect of the present invention involves said ultrasonic flaw detecting apparatus for inspecting a multi-layer structure, wherein the function generator outputs a pulse wave having at least two components of sine wave frequencies expressed by a ratio of integers to each other.

A sixth aspect of the present invention involves said ultrasonic flaw detecting apparatus for inspecting a multi-layer structure, wherein all of the sensors are mounted in a single probe shoe.

A seventh aspect of the present invention involves said ultrasonic flaw detecting apparatus for inspecting a multi-layer structure, wherein the medium is a liquid.

An eighth aspect of the present invention involves said ultrasonic flaw detecting apparatus for inspecting a multi-layer structure, wherein the medium is water.

A ninth aspect of the present invention involves said ultrasonic flaw detecting apparatus for inspecting a multi-layer structure, which further comprises a judging means for judging a sine wave frequency of the intensity detecting means at the time of detecting the lowest intensity; and a control means for receiving the judged result from the judging means and adjusting the output frequency of the function generator to the sine wave frequency at the time of detecting the lowest intensity.

A tenth aspect of the present invention involves an ultrasonic flaw detecting method, the method comprising the steps of transmitting an ultrasonic wave to a multi-layer structure, having a middle layer sandwiched between a first layer and a second layer, from the first layer while the frequency of the ultrasonic wave is varied, the middle layer having an acoustic impedance different from the acoustic impedances of both of the first and the second layers; receiving a boundary echo from the interface between the first layer and the middle layer every time the frequency is varied; detecting a received intensity of the boundary echo; receiving an echo from the inside of the second layer as an inspected result, when an ultrasonic wave having the frequency, at which the lowest level of received intensity is produced, is transmitted to the multi-layer structure; and recording or displaying the inspected result.

According to the first aspect, the sine wave frequency output from the function generator is determined by the frequency control means, an ultrasonic wave having the sine wave frequency is transmitted from the surface of the first layer into the multi-layer structure by the transmitting means, the ultrasonic wave is reflected at the interface between the first layer and the middle layer and becomes a boundary echo to be returned to the receiving means, and the intensity of the received boundary echo is detected by the intensity detecting means. This operation is repeated while the frequency of the ultrasonic wave is varied using the frequency control means, and an echo from the inside of the second layer is received as an inspected result when an ultrasonic wave having a frequency, at which the lowest level of the received intensity is produced, is transmitted to the multi-layer structure, and the inspected result is recorded or displayed.

According to the second aspect, the output of the function generator is amplified by the power amplifier to be applied to the first sensor, an ultrasonic wave from the first sensor is transmitted from the surface of the first layer into the multi-layer structure, the ultrasonic wave is reflected at the interface between the first layer and the middle layer and becomes a boundary echo to be returned to and detected by the second sensor and to be amplified by the second amplifier, and the intensity of the received boundary echo is detected by the intensity detecting means. This operation is repeated while the frequency of the ultrasonic wave is varied using the frequency control means, and an echo from the inside of the second layer is returned to and received by the third sensor when an ultrasonic wave having a frequency, at which the lowest level of the received intensity is produced, is transmitted to the multi-layer structure, the detected signal is received by the second amplifier as an inspected signal indicating the condition of the inside of the second layer and the inspected result is recorded or displayed.

According to the third aspect, the first sensor and the power amplifier are connected with a switching means, an output of the function generator is amplified by the power amplifier and applied to the first sensor, an ultrasonic wave from the first sensor is transmitted from the first layer into the multi-layer structure, the ultrasonic wave is reflected at the interface between the first layer and the middle layer and becomes a boundary echo to be returned to and detected by the second sensor and to be amplified by the second amplifier, and the intensity of the received boundary echo can be detected by the intensity detecting means. This operation is repeated while the frequency of the ultrasonic wave is varied using the frequency control means, and an echo from the inside of the second layer is returned to and received by the first sensor when an ultrasonic wave having a frequency, at which the lowest level of the received intensity is produced, is transmitted to the multi-layer structure; and by connecting the first sensor to the second amplifier using the switching means, the signal based on the echo returned to the first sensor is received by the second amplifier as an inspected signal indicating the condition of the inside of the second layer, and the inspected result is recorded or displayed.

According to the fourth aspect, the first sensor and the power amplifier are connected with a switching means, an output of the function generator is amplified by the power amplifier and applied to the first sensor, an ultrasonic wave from the first sensor is transmitted from the first layer into the multi-layer structure in a direction normal to the surface of the multi-layer structure, and after transmitting the ultrasonic wave, the first sensor is connected to the second amplifier using the switching means. The transmitted ultrasonic wave is reflected at the interface between the first layer and the middle layer and becomes a boundary echo to be returned in the normal direction to the first sensor and detected by the first sensor and to be amplified by the second amplifier, and the intensity of the received boundary echo can be detected by the intensity detecting means. This operation is repeated while the frequency of the ultrasonic wave is varied using the frequency control means, and as the frequency of the transmitted ultrasonic wave is changed so that the ultrasonic wave launched to the middle layer easily enters into the second layer, the intensity of the boundary echo from the interface is decreased so as to be detected by the intensity detecting means. When the intensity detecting means detects the lowest intensity, the first sensor is connected to the first amplifier by the switching means and an echo from the inside of the second layer, at the time when the ultrasonic wave having the frequency which produces the lowest intensity is transmitted to the multi-layer, is returned to the first sensor, the signal based on the echo returned to the first sensor is amplified by the second amplifier as an inspected signal indicating the condition of the inside of the second layer, and the inspected result is recorded or displayed.

According to the fifth aspect, in addition to the advantages obtained by any one of the first aspect to the fourth aspect, the ultrasonic wave energy passing in a round trip through the middle layer can be increased.

According to the sixth aspect, in addition to the advantages obtained by any one of the first aspect to the fourth aspect, all the sensors can be handled at the same time regardless of the total number of sensors, since all the sensors are mounted in a single probe shoe.

According to the seventh aspect, in addition to the advantages obtained by any one of the first aspect to the fourth aspect, efficient transmission of the transmitting ultrasonic wave and the echo through the middle layer can be obtained since the transmission coefficient of an ultrasonic wave for a liquid is higher than that for a gas.

According to the eighth aspect, in addition to the advantages obtained by any one of the first aspect to the fourth aspect, efficient transmission of the transmitting ultrasonic wave and the echo through the middle layer can be obtained by using water for the medium.

According to the ninth aspect, in addition to the advantages obtained by any one of the first aspect to the fourth aspect, the judging means judges a sine wave frequency indicating the lowest intensity among intensities of various frequencies detected by the intensity detecting means, and the control means controls the function generator so as to output the judged frequency, and so the operating frequency of the ultrasonic wave can be automatically and efficiently set.

According to the tenth aspect, the ultrasonic wave transmitted to the multi-layer structure from the surface of the first layer is reflected by the interface between the first layer and the second layer and is received as a boundary echo, and the intensity of the boundary echo can be detected by the intensity detecting means. This operation is repeated while the output frequency from the function generator is varied using the frequency control means. When the intensity detecting means detects the lowest intensity, that is, when the ultrasonic wave is transmitted from the interface into the middle layer and the intensity of the echo is decreased, an echo from the inside of the second layer obtained by transmitting an ultrasonic wave having the frequency at that time into the multi-layer structure can be received as an inspected signal.

DETAILED DESCRIPTION OF THE PREFERRED EMBODIMENTS

Figure 7:
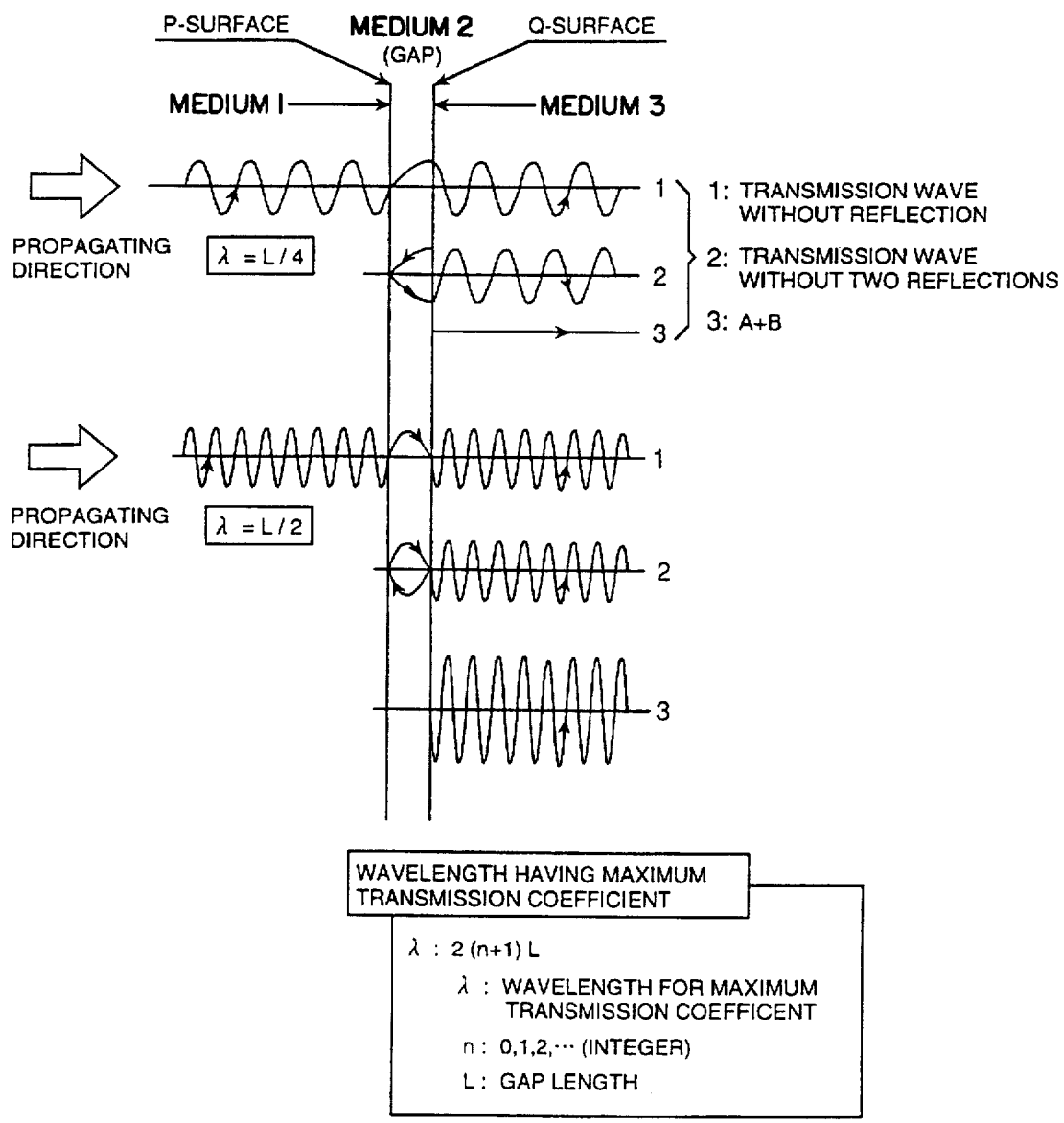
FIG. 7 is a diagram showing the interference principle of an ultrasonic wave.

FIG. 7 is a view which aids in explaining the principle of operation based on an embodiment in accordance with the present invention.

FIG. 7 is a schematic view of a case where there is a gap between two steel plates. A case is assumed where an ultrasonic wave used for an ultrasonic wave flaw detecting apparatus propagates from a medium 1 and then propagates in a medium 3 after passing through a medium 2.

The ultrasonic wave is reflected at an interface between the medium 1 and the medium 2, and is further reflected at an interface between the medium 2 and the medium 3.

However, in a first case, where the gap width is one-fourth of the wavelength of the ultrasonic wave, the ultrasonic wave transmitted through the gap between the medium 2 and the medium 3 is 180° out of phase with the round-trip ultrasonic wave reflected in the gap, and so the both ultrasonic waves cancel each other while propagating in the medium 3.

However, in a second case, where the gap width is one-half of the wavelength of the ultrasonic wave, the ultrasonic wave transmitted through the gap between the medium 2 and the medium 3 is in phase with the round-trip ultrasonic wave reflected in the gap, and so both ultrasonic waves strengthen each other while propagating in the medium 3.

The phenomenon will be explained below, using equations.

Equation 1 is a transmission coefficient of the interface between the medium 1 and the medium 2 when an ultrasonic wave propagates from the medium 1 to the medium 2.

$$T_{ij} = 2 Z_i / (Z_i + Z_j) \qquad (1)$$

$T_{ij}$: transmission coefficient of the interface between the medium i and the medium j $Z_i$: acoustic impedance ($\rho_i \times V_i$)

$\rho_i$: density of medium i $V_i$: wave velocity of medium i

Therein, Z is an acoustic impedance of a medium in which an ultrasonic wave propagates, and is expressed by the product of the density of the medium and the wave velocity in the medium.

When the ultrasonic wave propagates through the medium 2 to the medium 3 from the medium 1, the ultrasonic wave is multitudinously reflected by the two interfaces between the medium 1 and the medium 2 and between the medium 2 and the medium 3.

Therein, letting the interval between the two interfaces be L, the composite transmission coefficient from the medium 1 to the medium 3 taking the two interfaces into consideration can be expressed by Equation 2.

$$T_T = \frac{2Z_2(Z_1 Z_3)^{-1/2}}{Z_2(Z_3 + Z_1)\cos(2\pi L/\lambda) + i(Z_2^2 + Z_1 Z_3)\sin(2\pi L/\lambda)} \qquad (2)$$

$T_T$: composite transmission coefficient between the two interfaces

L: propagation length of a wave in the medium 2 between the two interfaces $\lambda$: wavelength of a wave propagating in the medium 2 between the two interfaces i: imaginary number.

It can be Understood from Equation 2 that the composite transmission coefficient can be made 1 (one) by setting the wavelength of the ultrasonic wave properly.

That is, the condition is that twice the propagation length of the ultrasonic wave in the gap between the two interfaces becomes an integral number of times the wavelength of the wave propagating in the medium 2.

The frequency of the ultrasonic wave at that time can be calculated from Equation 3.

$$f=(n+1)v/2L \quad (3)$$

f: frequency of the wave transmitting in the gap
v: velocity of the wave propagating in a medium filling the gap
L: propagation length of the wave propagating in the gap
n: an integer That is, an ultrasonic wave can be efficiently propagated in a layer in which it is difficult for the ultrasonic wave to propagate, such as a gap, by varying the frequency of the ultrasonic wave corresponding to the propagation length of the gap in which the ultrasonic wave propagates, so that twice the propagation length of the ultrasonic wave in the gap between the two interfaces is adjusted to become an integral number of times the wavelength of the wave propagating in the medium 2.

Therefore, when the ultrasonic wave can pass across the layer in which it is difficult for the ultrasonic wave to be propagated, such as a gap, a flaw existing at a place beyond the gap can be detected.

That is, the energy of the ultrasonic wave can be efficiently used for inspection of a flaw by making the frequency of the ultrasonic wave to be used for flaw detection coincide with the condition that the ultrasonic wave can pass across a layer in which it is difficult for the ultrasonic wave to propagate.

Embodiments of the present invention will be described in detail below, referring to the accompanying figures.

Figure 1:
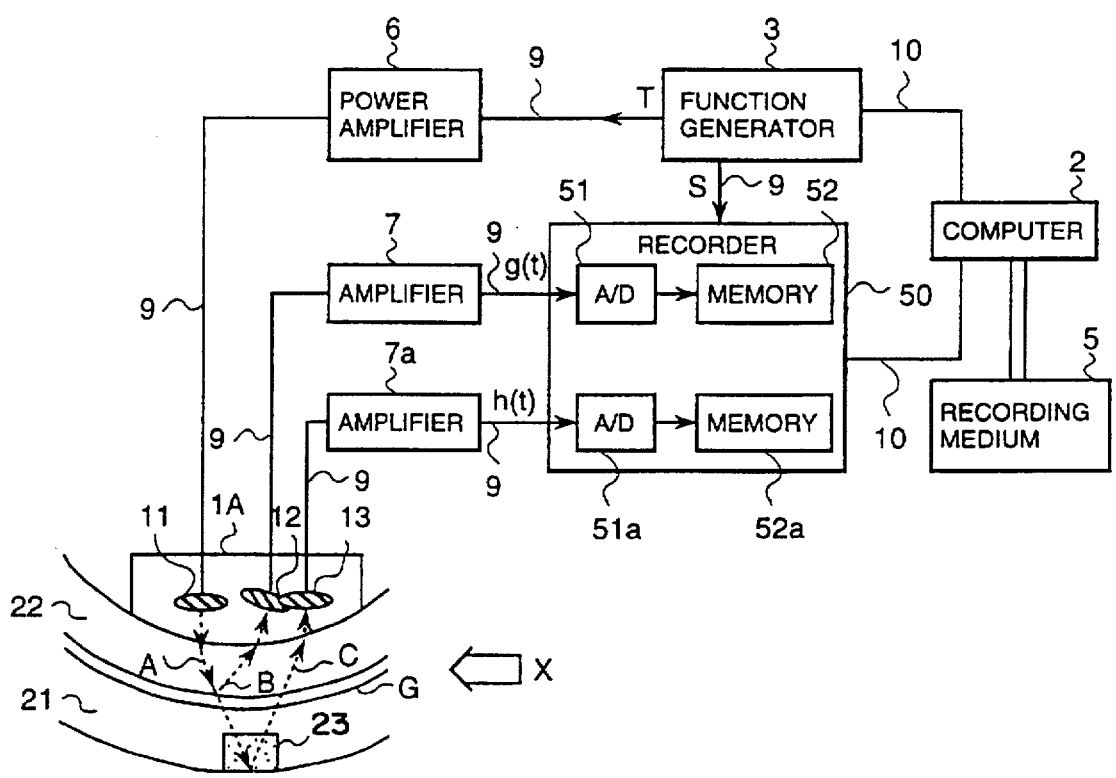
FIG. 1 is a block diagram showing the overall construction of a first embodiment of an ultrasonic flaw detecting apparatus in accordance with the present invention.
Figure 2:
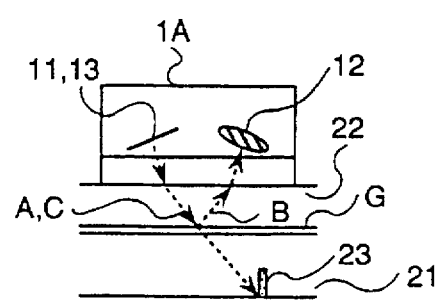
FIG. 2 is a diagram showing the flaw detection as seen in the direction of an arrow X in FIG. 1.

FIG. 1 and FIG. 2 show a first embodiment in accordance with the present invention.

FIG. 1 is a block diagram showing the first embodiment of an ultrasonic flaw detecting apparatus in accordance with the present invention. FIG. 2 is a view seen in the direction of an arrow X in FIG. 1.

Figure 3:
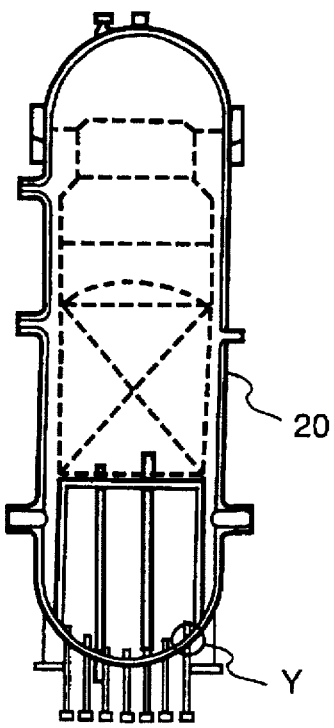
FIG. 3 is a cross-sectional view of a BWR pressure vessel.
Figure 4:
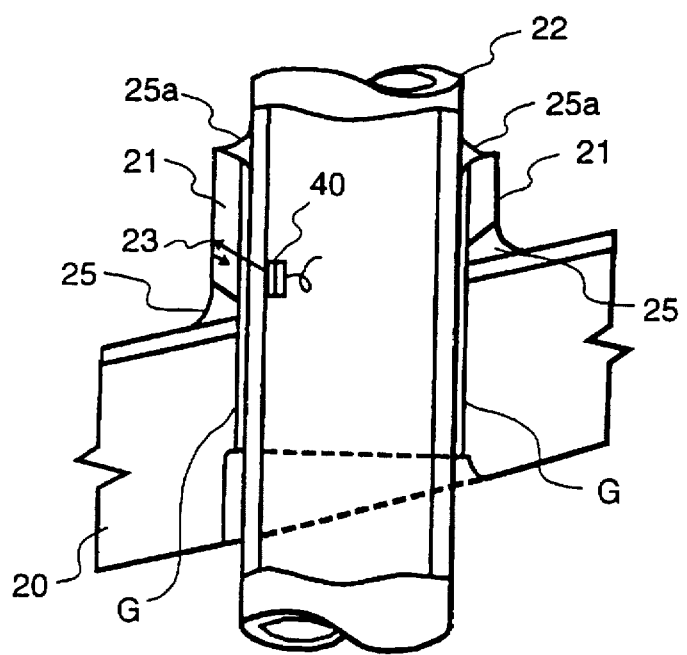
FIG. 4 is an enlarged view of the portion Y of FIG. 3 which is a portion inspected by conventional technology.
Figure 5:
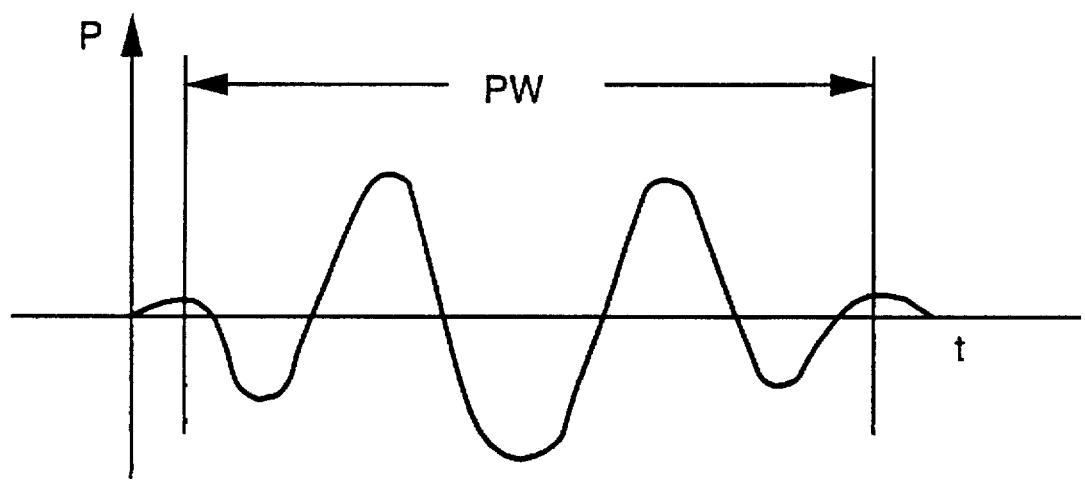
FIG. 5 is a wave diagram showing an ultrasonic wave used in an inspection according to conventional technology.
Figure 6:
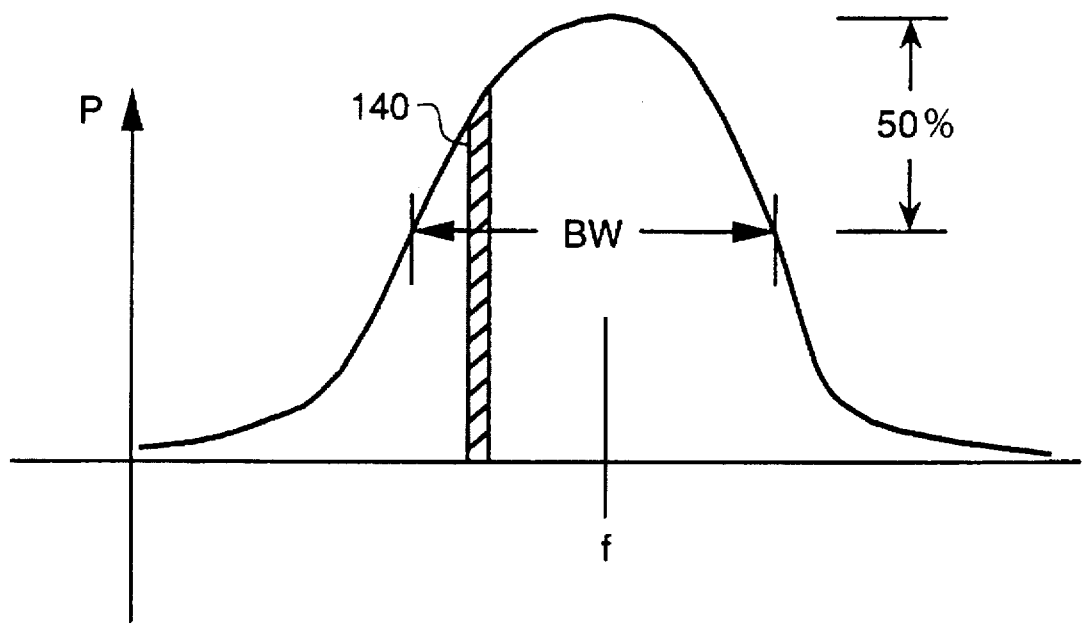
FIG. 6 is a diagram showing the spectrum of an ultrasonic wave used in an inspection according to conventional technology.

As an example of a multi-layer structure of an object to be inspected, on which ultrasonic wave flaw detection is performed, a control rod drive (CRD) housing 22 and a stub-tube 21 in the bottom head of a pressure vessel of a boiling water reactor (BWR) shown in FIG. 3 and FIG. 4 is selected.

There exists a gap G between the CRD housing 22 and the stub-tube 21. The gap G has a width of approximately 0.1 mm which is filled with air and has an acoustic impedance largely different from the acoustic impedances of the adjacent stub-tube 21 and the adjacent CRD housing 22.

The ultrasonic wave flaw detecting apparatus of the first embodiment, as shown in FIG. 1 and FIG. 2, is composed of a first sensor 11 for launching an ultrasonic wave into the CRD housing 22 along a path A in a slanting direction with respect to the gap G, a function generator 3 for outputting a pulse-shaped sine wave T and a timing signal S, a power amplifier 6 for amplifying and supplying the pulse-shaped sine wave to the first sensor 11, a second sensor 12 arranged at a position capable of receiving a bottom echo of the CRD housing 22 reflected along a path B, an amplifier 7 for amplifying a received signal of the second sensor 12, a third sensor 13 arranged in a position capable of receiving a flaw echo reflected along a path C from a circumferential direction flaw 23 existing on the bottom surface of the stub-tube 21, that is, in the circumferential direction of the first sensor 11, an amplifier 7a for amplifying a received signal of the third sensor 13, a recorder 50 formed of A/D converters 51, 51a and memories 52, 52a, a computer 2 for controlling the function generator 3 and the recorder 50 through a GPIB cable 10, and a recording medium 5. The first sensor 11 and the power amplifier 6, the second sensor 12 and the amplifier 7, the third sensor 13 and the amplifier 7a, the power amplifier 6 and the function generator 3, the function generator 3 and the recorder 50, and the amplifiers 7, 7a and the recorder 50 are connected with coaxial cables 9, respectively.

The function generator 3 and the computer 2, and the recorder 50 and the computer 2 are connected with GPIB cables 10, respectively.

As the function generator 3, a device capable of outputting a pulse-shaped sine wave, for example, AWG2040, a product of Tektronix Co., is used.

A computer having a GPIB interface is used as the computer.

Figure 8:
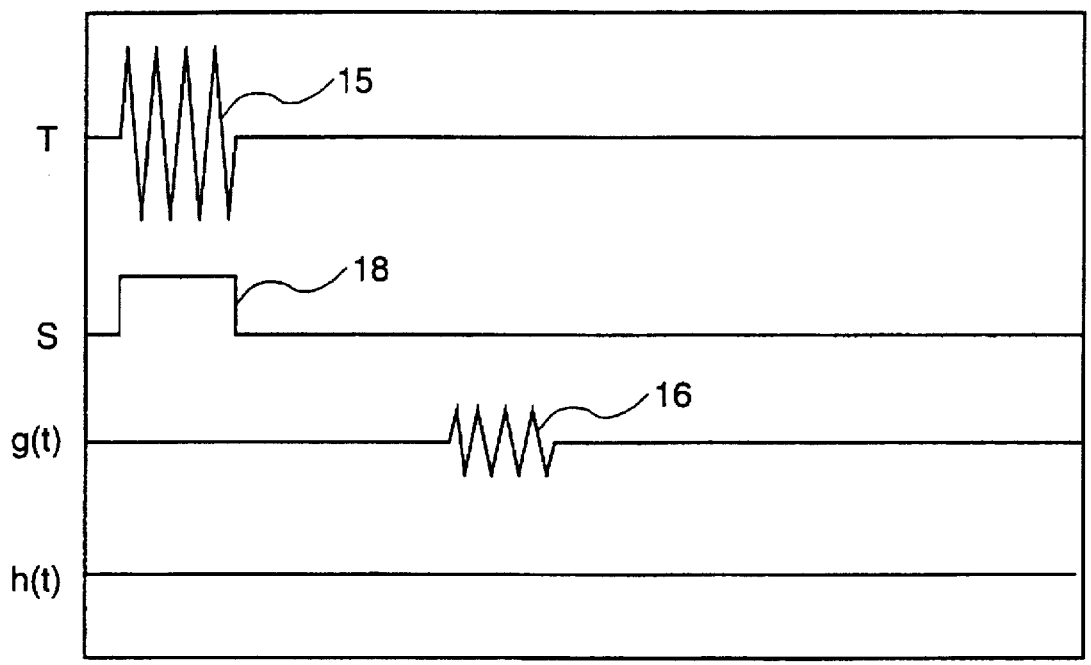
FIG. 8 is a waveform chart of signals T, S, g(t), h(t) in a first embodiment where an ultrasonic wave is not transmitted across a gap.
Figure 9:
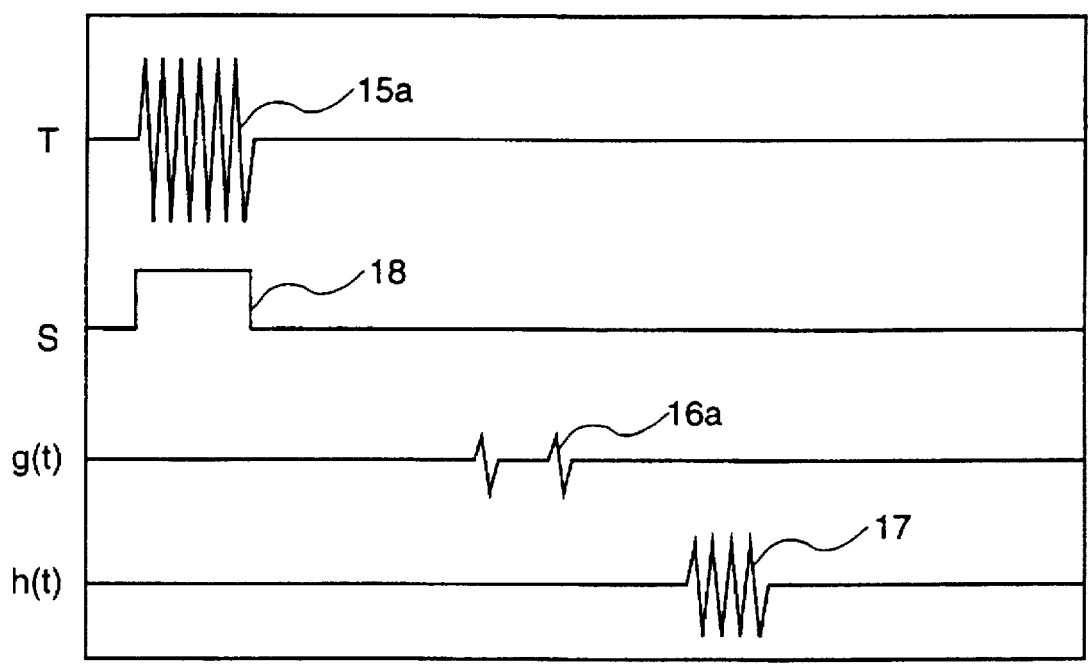
FIG. 9 is a waveform chart of signals T, S, g(t), h(t) in a first embodiment where an ultrasonic wave is transmitted across a gap.

FIG. 8 and FIG. 9 time-sequentially show an output signal T and a timing signal S output from the function generator 3 and output signals g(t) and h(t) of the amplifiers 7, 7a. A pulse-shaped sine wave 15 applied to the first sensor, bottom echoes 16, 16a of the CRD housing received by the second sensor 12, a flaw echo 17 reflected from a circumferential flaw 23 received by the third sensor are shown.

Figure 10:
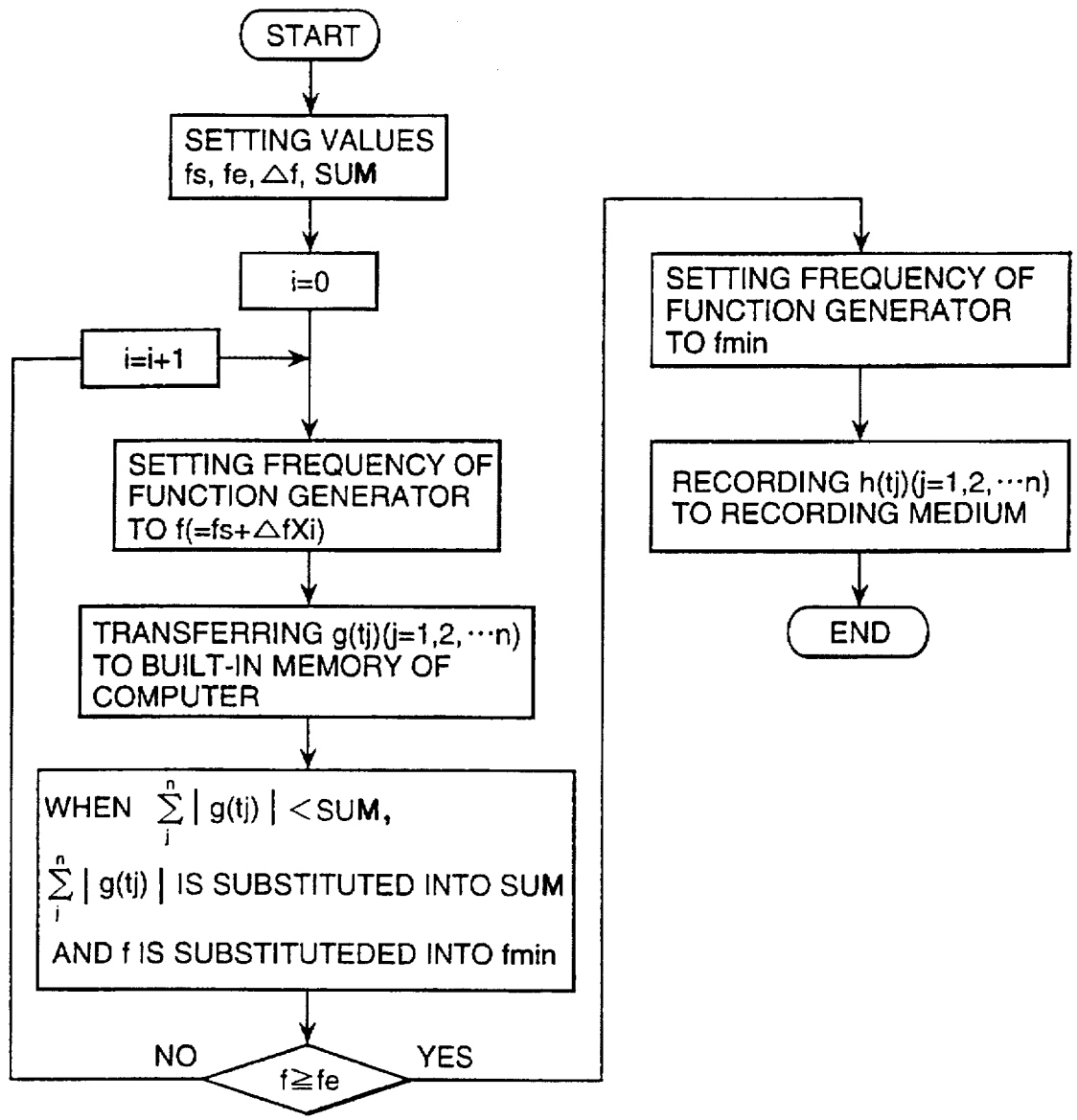
FIG. 10 is a flow chart showing a control algorithm of the first embodiment.

FIG. 10 shows a control algorithm indicating how the computer 2 controls the function generator 3 and the recorder 50 and what calculation the computer performs.

The inspection procedure will be described below.

Initially, a probe 1A composed of the first, the second and the third sensors is arranged on the inner surface of the CRD housing 22.

Values $f_s$ (a frequency given first), fe (a frequency given last), $\Delta f$ (one unit of frequency variation), SUM (arbitrary value) in the control program are set by the internal control of the program or by an external input unit, such as a keyboard.

The function generator 3 receives a command from the computer 2 through the GPIB cable 10, and outputs the pulse-shaped sine wave 15 having a sine wave frequency $f_s$ and the timing pulse 18 at the same time. The recorder 50 performs A/D converting of the signals g(t), h(t) using the A/D converters 51, 51a when detecting the leading edge of the timing pulse 18, and records them in built-in memories 52, 52a.

After the pulse-shaped sine wave 15 is amplified using the power amplifier 6, the pulse-shaped sine wave is applied to the first sensor 11 to launch an ultrasonic wave into the CRD housing along the path A.

A bottom echo 16 of the CRD housing 22 is received by the second sensor 12.

The received bottom echo 16 is amplified using the amplifier 7.

The amplified bottom echo 16 is input to the recorder 50.

The recorder 50 performs A/D converting of the bottom echo 16 using the A/D converter 51 and stores it into the built-in memory 52.

The computer 2 transfers n items of data $g(t_j)$ (j=1, 2, . . . , n) stored in the built-in memory 52 to a built-in memory of the computer 2.

Absolute values of the data $g(t_j)$ (j=1, 2, . . . , n) summed by the computer 2.

When the summed value is smaller than SUM, the summed value is substituted into SUM and the sine wave frequency at that time is substituted into $f_{min}$.

Again, the function generator 3 receives a command from the computer 2 through the GPIB cable 10, and outputs the pulse-shaped sine wave 15 having a sine wave frequency $f_s+\Delta f$ and the timing pulse 18 at this time. And, the same signal processing and calculation are performed.

By increasing the sine wave frequency as $f_s$, $f_s+\Delta f$, $f_s+2\Delta f$, ..., $f_c$ as described above, a frequency $f_{min}$ when the summed value of the data $g(t_j)$ (j=1, 2, ..., n) becomes minimum can be obtained.

When the summed value becomes a minimum, the bottom echo 16 in FIG. 8 changes to the bottom echo 16a in FIG. 9. That is, the obtained $f_{min}$ is the frequency when the ultrasonic wave passes through the gap.

The function generator 3 receives a command from the computer 2 through the GPIB cable 10, and outputs the pulse-shaped sine wave 15 having a sine wave frequency $f_{min}$ and the timing pulse 18.

The pulse-shaped sine wave 15a passes through the gap, and the flaw echo 17 is received by the third sensor 13 and appears in the signal h(t) as shown in FIG. 9.

The computer 2 transfers n items of data $h(t_j)$ (j=1, 2, ..., n) stored in the built-in memory 52a to the built-in memory of the computer 2.

The computer 2 records the data $h(t_j)$ (j=1, 2, ..., n) in the recording medium 5, such as a floppy disk.

The flaw echo 17 is identified from the data $h(t_j)$ (j=1, 2, ..., n).

In the aforementioned algorithm, the frequency $f_{min}$ at which the ultrasonic wave passes through the gap is determined by comparing the summed values of the absolute valves of $g(t_j)$ (j=1, 2, ..., n). Since the change in the bottom echo from 16 to 16a is evidence that the ultrasonic wave passes through the gap, there can be considered other methods of obtaining $f_{min}$ such as counting the local minimum of the bottom echo, pattern recognition of the bottom echo and so on.

Figure 11:
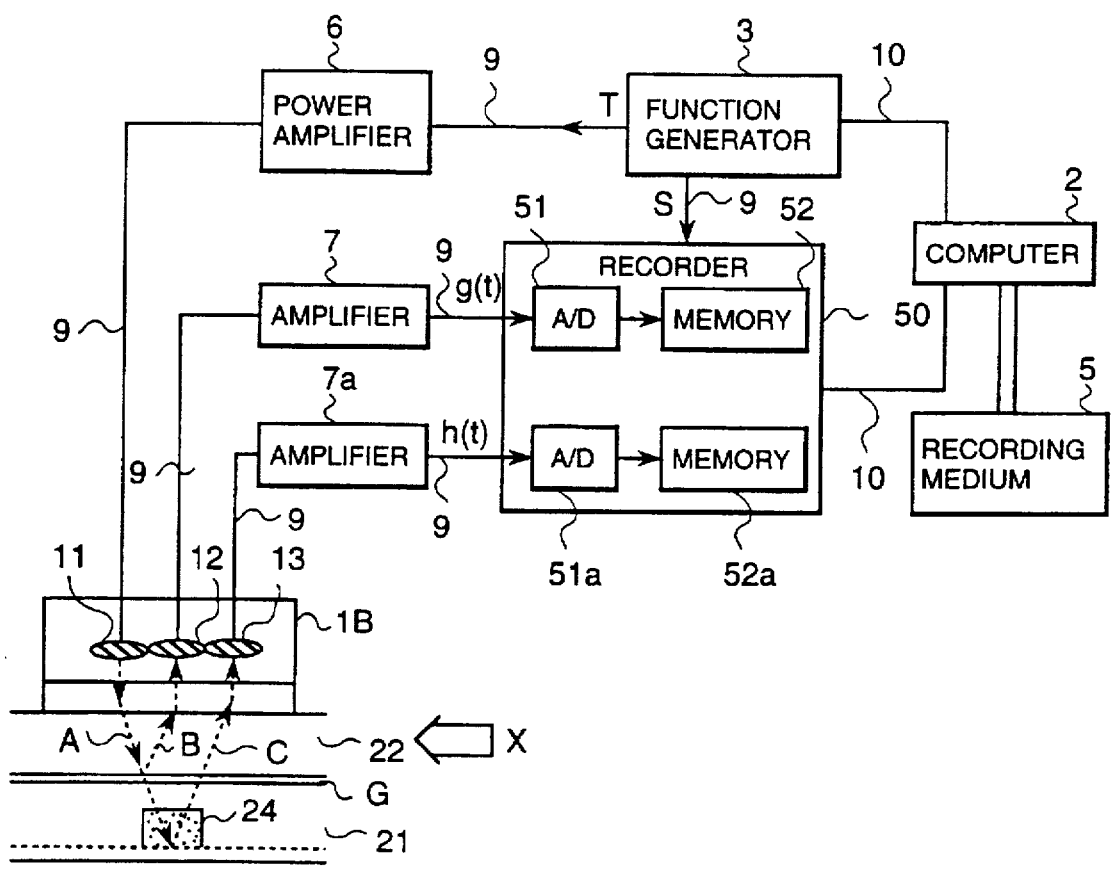
FIG. 11 is a block diagram showing the overall construction of a second embodiment of an ultrasonic flaw detecting apparatus in accordance with the present invention.
Figure 12:
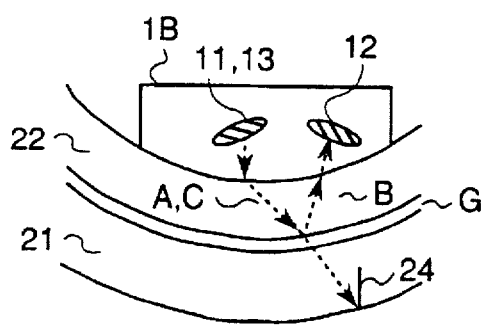
FIG. 12 is a diagram showing the flaw detection as seen in the direction of an arrow X in FIG. 11.

FIG. 11 and FIG. 12 are a second embodiment in accordance with the present invention to realize detection of an axial direction flaw.

FIG. 11 is a block diagram showing the second embodiment of an ultrasonic flaw detecting apparatus, and FIG. 12 is a is a view seen in the direction of an arrow X in FIG. 11.

The difference between the second embodiment and the first embodiment is in the probe. The waveforms T, S, g(t), h(t) and the control algorithm in the second embodiment are the same in as FIG. 8, FIG. 9 and FIG. 10.

In the second embodiment, the third sensor 13 in the first embodiment of FIG. 1 and FIG. 2 is arranged at a position capable of receiving the reflected echo of the axial direction flaw on the outer surface of the stub-tube 21, that is, at a position of the axial direction of the first sensor 11.

By using the probe 1B having the three sensors 11, 12, 13 arranged as described above, the axial direction flaw 24 on the outer surface of the stub-tube can be detected.

Figure 13:
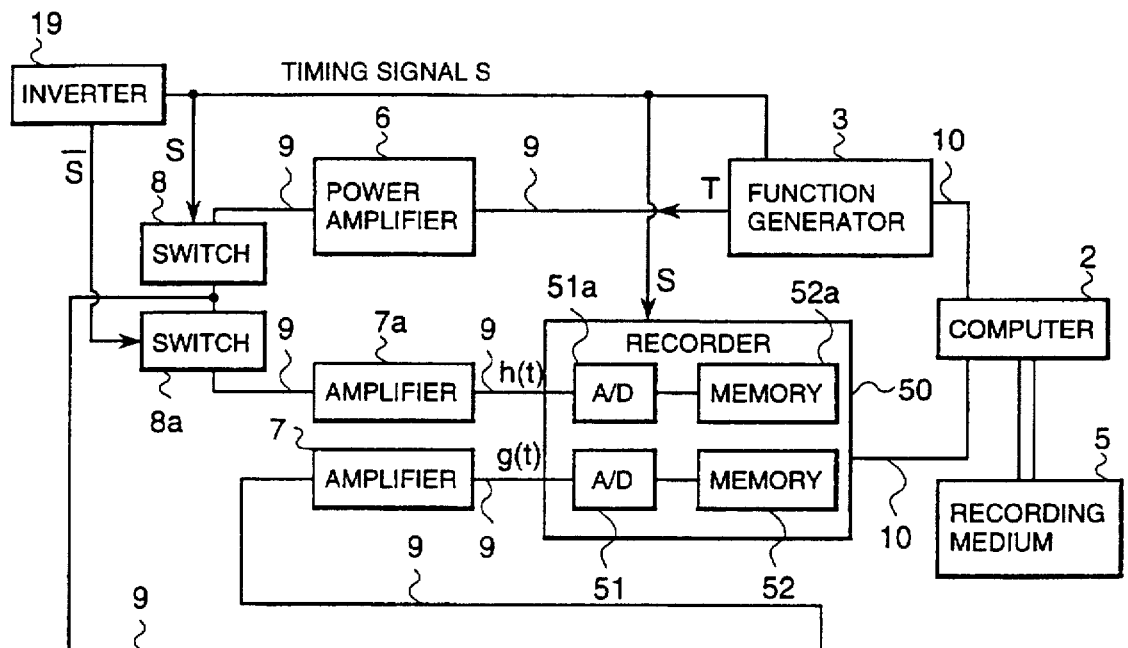
FIG. 13 is a block diagram showing the overall construction of a third embodiment of an ultrasonic flaw detecting apparatus in accordance with the present invention.
Figure 13:
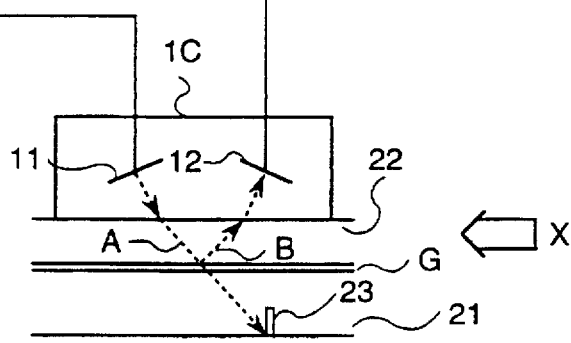
Figure 14:
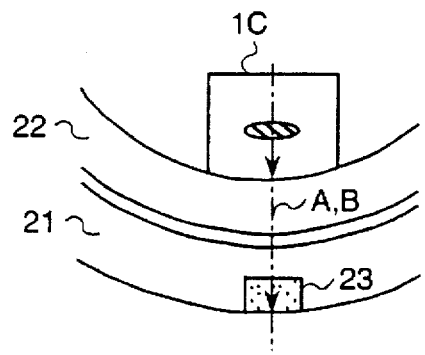
FIG. 14 is a diagram showing the flaw detection as seen in the direction in an arrow X in FIG. 13.

FIG. 13 and FIG. 14 are a third embodiment in accordance with the present invention to realize detection of a circumferential direction flaw. FIG. 13 is a block diagram showing the third embodiment of an ultrasonic flaw detecting apparatus, and FIG. 14 is a view seen in the direction of an arrow X in FIG. 13.

The differences between the third embodiment and the first embodiment are in the probe and in the construction of the apparatus. The waveforms T, S, g(t), h(t) and the control algorithm in the third embodiment are the same as in FIG. 8, FIG. 9 and FIG. 10.

The ultrasonic wave flaw detecting apparatus of the third embodiment, as shown in FIG. 13 and FIG. 14, is composed of a first sensor 11 for launching an ultrasonic wave along a path A parallel to the axial direction of the CRD housing 22 and in a slanting direction to the gap G and for receiving an echo reflected from a circumferential direction flaw 23 existing on the outer surface of the stub-tube 21, a function generator 3 for outputting a pulse-shaped sine wave T and a timing signal S, a power amplifier 6 for amplifying and supplying the pulse-shaped sine wave to the first sensor 11, a second sensor 12 arranged at a position capable of receiving a bottom echo of the CRD housing 22 reflected along a path B, an amplifier 7 for amplifying a received signal of the second sensor 12, an amplifier 7a for amplifying a received signal of the first sensor 11, a recorder 50 formed of A/D converters 51, 51a and memories 52, 52a, an inverter 19 for reversing the timing signal S, switches 8, 8a for switching the first sensor 11 between the power amplifier 6 and the amplifier 7a, a computer 2 for controlling the function generator 3 and the recorder 50 through a GPIB cable 10, and a recording medium 5.

The first sensor 11 and the switches 8, 8a, the switch 8 and the power amplifier 6, the switch 8a and the amplifier 7a, the second sensor 12 and the amplifier 7, the power amplifier 6 and the function generator 3, the function generator 3 and the recorder 50, the function generator 3 and the switch 8, the function generator 3 and the inverter 19, the inverter 19 and the switch 8a, and the amplifiers 7, 7a and the recorder 50 are connected with coaxial cables 9, respectively.

The function generator 3 and the computer 2, and the recorder 50 and the computer 2 are connected with GPIB cables 10, respectively.

In the third embodiment, the pulse width of the timing pulse 18 is set to be larger than the pulse width of the pulse-shaped sine wave 15. The switches 8, 8a are switched to the ON state when the timing pulses S, $\overline{S}$ are in a HIGH state.

By adjusting the timing signal S, as described above, using the inverter and the switch, the first sensor 11 is connected to the power amplifier 6 while the function generator is serving to output a pulse-shaped sine wave, and during the other period, the first sensor 11 is connected to the amplifier 7a.

By forming the apparatus in the manner described above, a circumferential direction flaw existing in various depths of the stub-tube 21 can be detected using a probe 1C composed of only two sensors.

Figure 15:
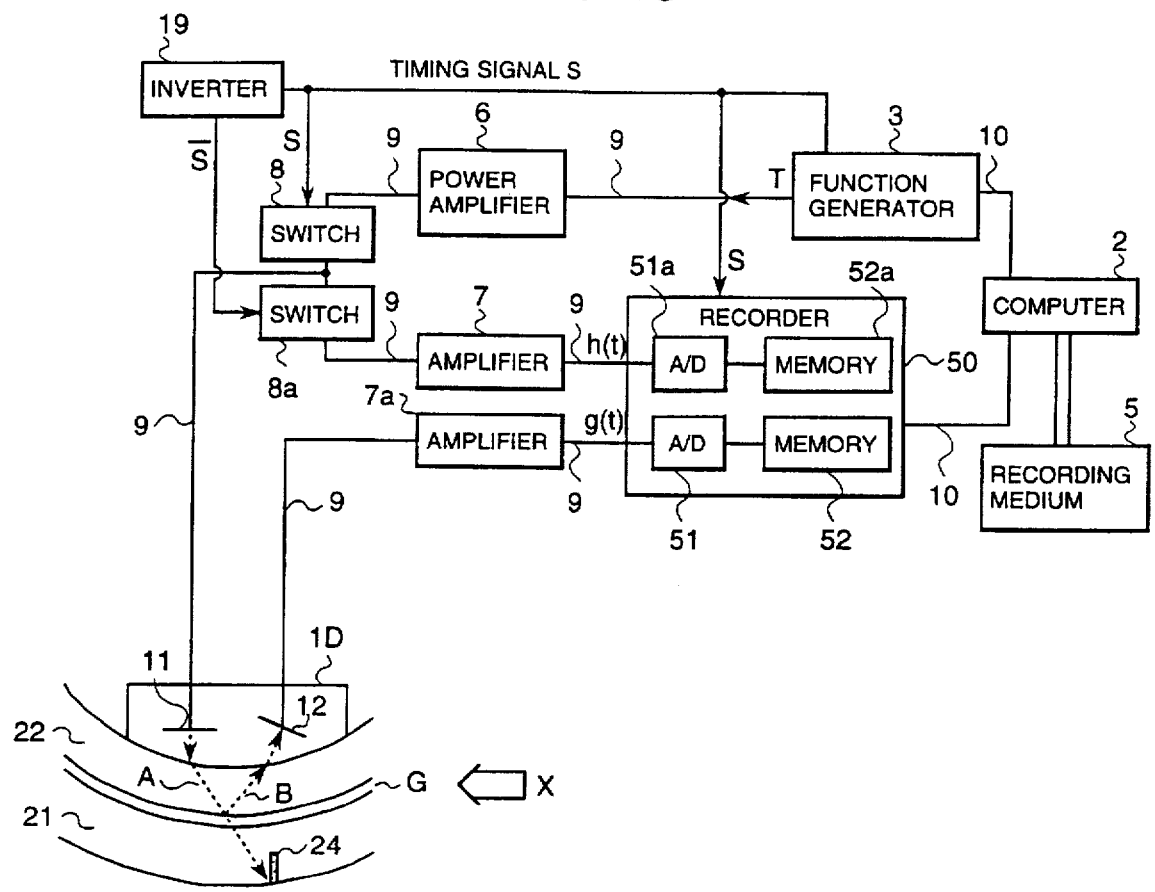
FIG. 15 is a block diagram showing the overall construction of a fourth embodiment of an ultrasonic flaw detecting apparatus in accordance with the present invention.
Figure 16:
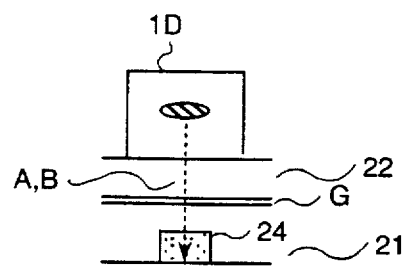
FIG. 16 is a diagram showing the flaw detection as seen in the direction of an arrow X in FIG. 15.

A fourth embodiment according to the present invention shown in FIG. 15 and FIG. 16 can detect an axial direction flaw existing in various depths of the stub-tube 21 using only two sensors. FIG. 15 is a block diagram showing the fourth embodiment of an ultrasonic flaw detecting apparatus. FIG. 16 is a view seen in the direction of an arrow X of FIG. 15.

The waveforms T, S, g(t), h(t) and the control algorithm in the fourth embodiment are the same as in FIG. 8, FIG. 11 and FIG. 10.

In the fourth embodiment, the first sensor 11 launches an ultrasonic wave into the CRD housing 22 along a path A normal to the axial direction and is arranged at a position capable of receiving a reflected echo from an axial direction flaw 24 existing on the outer surface of the stub-tube 21. The sensor 12 is arranged in the circumferential direction of the first sensor.

By using a probe 1D having the two sensors 11 and 12 arranged as described above, an axial direction flaw 24 on the stub-tube 21 can be detected.

The other elements are the same as those in the third embodiment.

Figure 17:
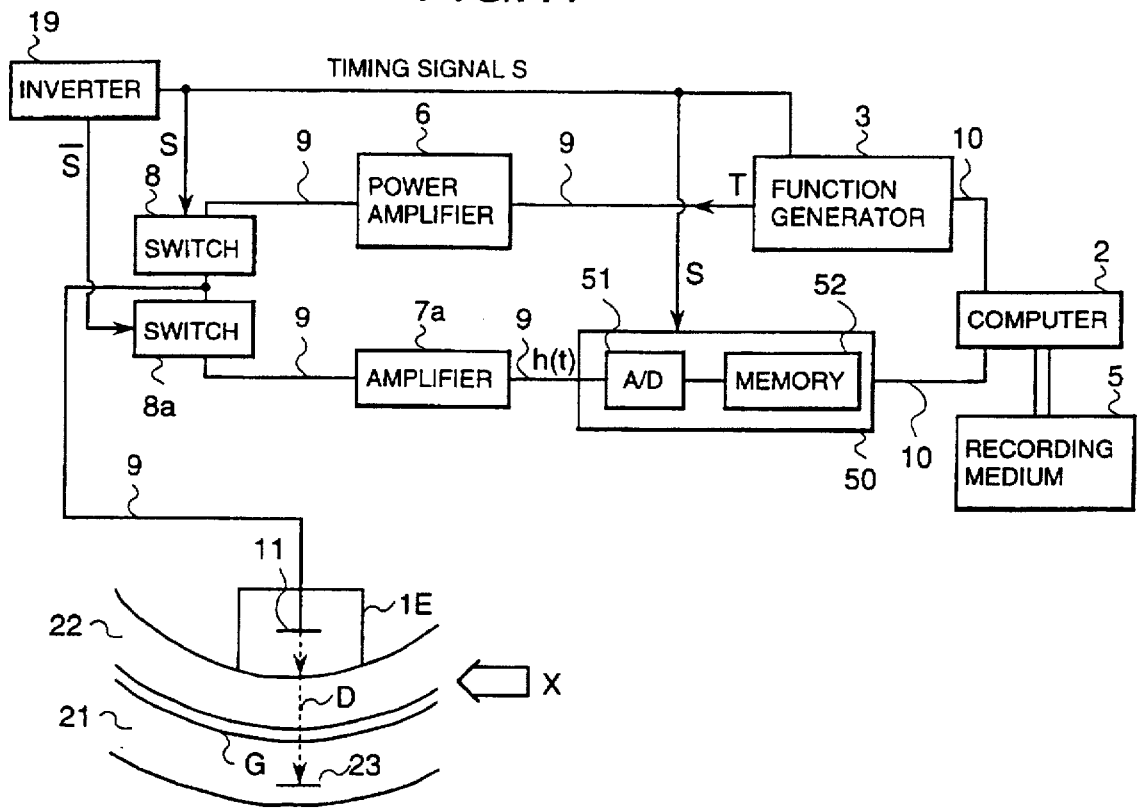
FIG. 17 is a block diagram showing the overall construction of a fifth embodiment of an ultrasonic flaw detecting apparatus in accordance with the present invention.
Figure 18:
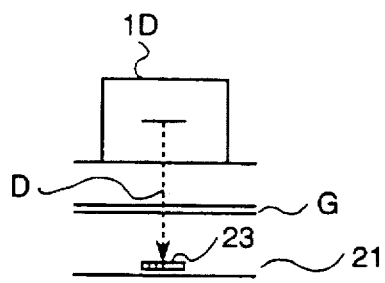
FIG. 18 is a diagram showing the flaw detection as seen in the direction of an arrow X in FIG. 16.

A fifth embodiment according to the present invention shown in FIG. 17 and FIG. 18 has one sensor which launches an ultrasonic wave in a direction normal to the wall surface of the CRD housing 22.

FIG. 17 is a block diagram showing the fifth embodiment of an ultrasonic flaw detecting apparatus. FIG. 18 is a view seen in the direction of the arrow X in FIG. 17.

The ultrasonic wave flaw detecting apparatus of the fifth embodiment, as shown in FIG. 17 and FIG. 18, is composed of a first sensor 11 for launching an ultrasonic wave along a path D perpendicular to the wall surface of the CRD housing 22, a function generator 3 for outputting a pulse-shaped sine wave and a timing signal S, a power amplifier 6 for amplifying and supplying the pulse-shaped sine wave to the first sensor 11, an amplifier 7 for amplifying a received signal of the first sensor 11, a recorder 50 formed of an A/D converter 51 and a memory 52, an inverter 19 for inverting the timing signal S, switches 8, 8a for switching the first sensor 11 between the power amplifier 6 and the amplifier 7, a computer 2 for controlling the function generator 3 and the recorder 50 through a GPIB cable 10, and a recording medium 5.

The first sensor 11 and the switches 8, 8a, the switch 8 and the power amplifier 6, the switch 8a and the amplifier 7, the power amplifier 6 and the function generator 3, the amplifier 7 and the recorder 50, the function generator 3 and the recorder 50, the function generator 3 and the inverter 19, the function generator 3 and the switch 8, and the inverter 19 and the switch 8a, are connected with coaxial cables 9, respectively.

The function generator 3 and the computer 2, and the recorder 50 and the computer 2, are connected with GPIB cables 10, respectively.

Figure 19:
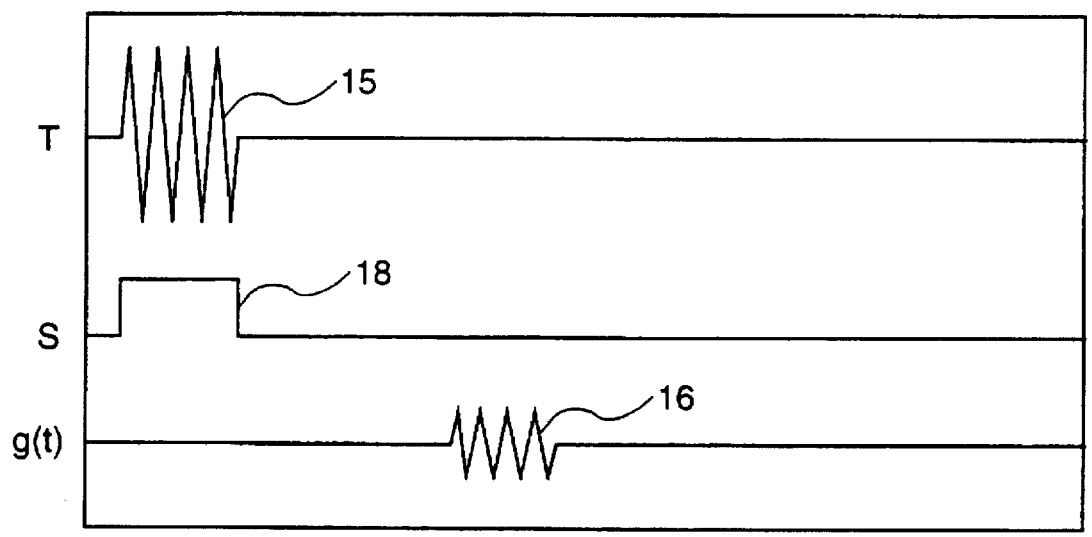
FIG. 19 is a waveform chart of signals T, S, g(t) in the fifth embodiment where an ultrasonic wave is not transmitted across a gap.
Figure 20:
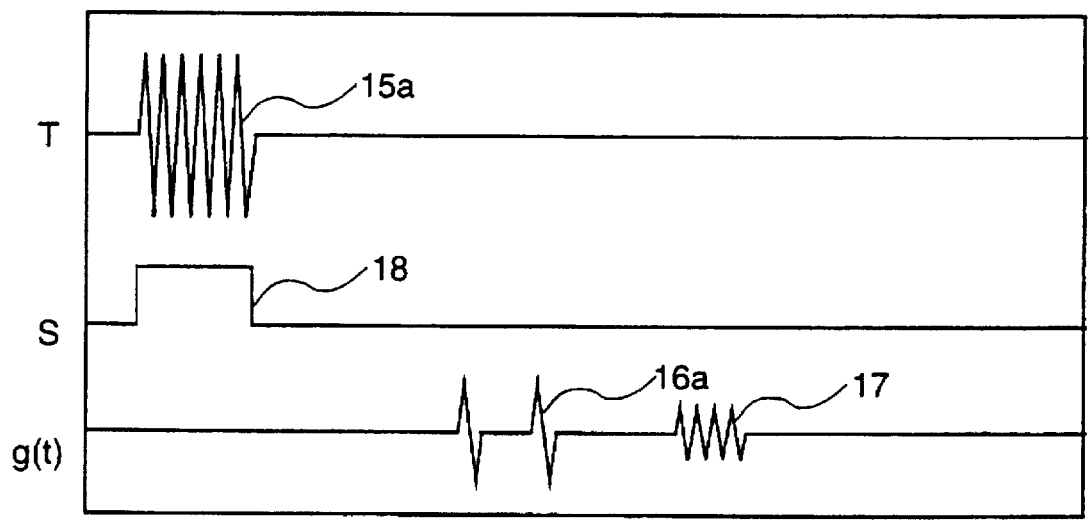
FIG. 20 is a waveform chart of signals T, S, g(t) in the fifth embodiment where an ultrasonic wave is transmitted across a gap.

FIG. 19 and FIG. 20 time-sequentially show an output signal T and a timing signal S output from the function generator 3 and an output signal g(t) of the amplifier 7. A pulse-shaped sine wave 15 applied to the first sensor, bottom echoes 16, 16a of the CRD housing received by the first sensor 11, and a flaw echo 17 reflected from a flaw 23 are also shown.

Figure 21:
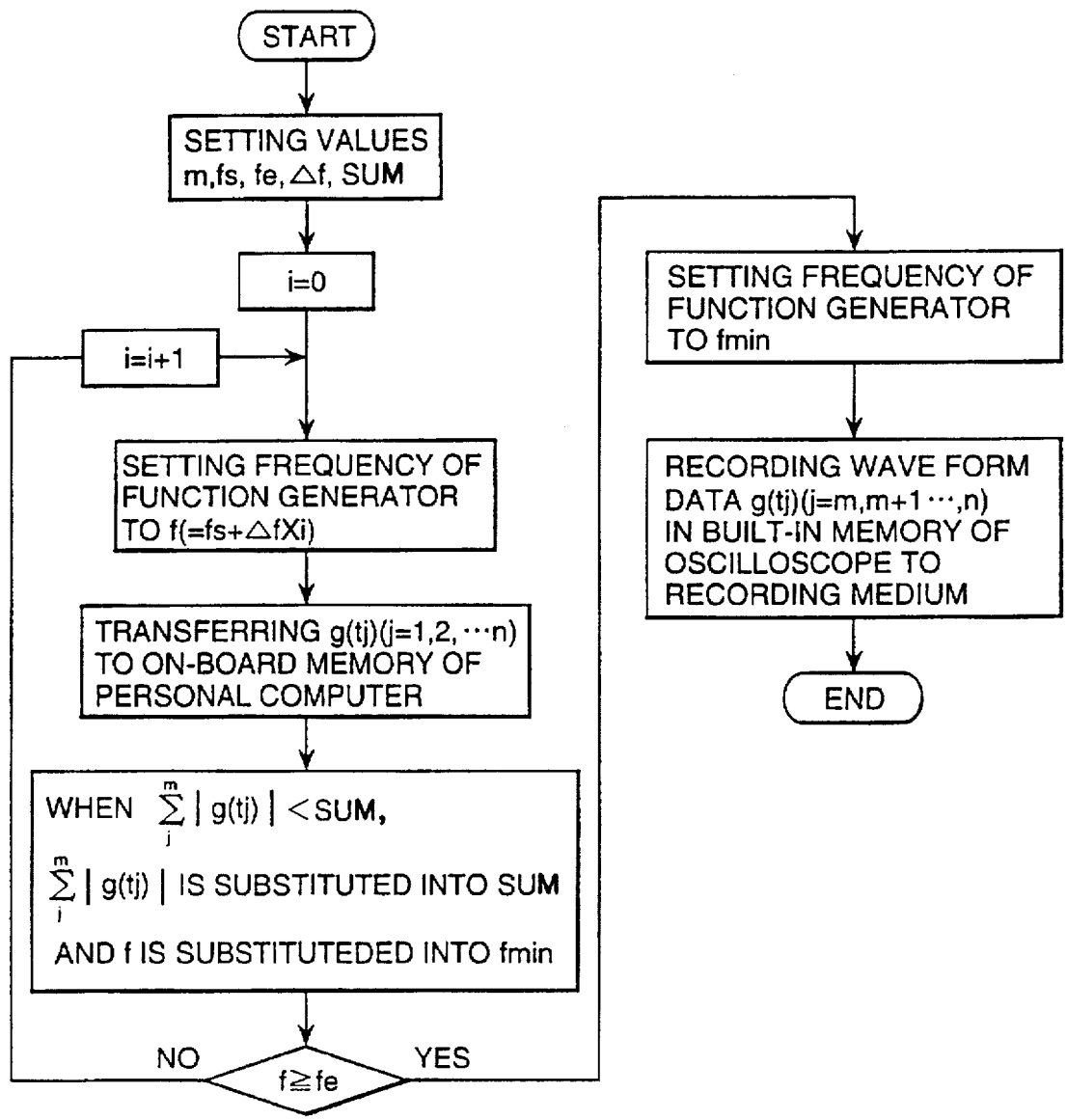
FIG. 21 is a flow chart showing a control algorithm of the fifth embodiment.

FIG. 21 shows a control algorithm indicating how the computer 2 controls the function generator 3 and the recorder 50 and what calculation the computer performs.

The inspection procedure will be described below.

Initially, a probe 1E composed of the first sensor is arranged on the inner surface of the CRD housing 22.

Values $f_s$, fe, $\Delta f$, SUM in the control program are set by the internal control of the program or by an external input unit, such as a keyboard.

The function generator 3 receives a command from the computer 2 through the GPIB cable 10, and outputs the pulse-shaped sine wave 15 at the sine wave frequency $f_s$ and the timing pulse 18 at the same time. The recorder 50 performs A/D conversion of the signal g(t) using the A/D converter 51 when detecting the leading edge of the timing pulse 18, and records it in a built-in memory 52.

After the pulse-shaped sine wave 15 is amplified using the power amplifier 6, the pulse-shaped sine wave is applied to the first sensor 11 to launch an ultrasonic wave into the CRD housing along the path D.

A bottom echo 16 of the CRD housing 22 is received by the first sensor 11.

The received bottom echo 16 is amplified using the amplifier 7.

The amplified bottom echo 16 is input to the recorder 50.

The recorder 50 performs A/D conversion of the bottom echo 16 using the A/D converter 51 and stores it into the built-in memory 52.

The computer 2 transfers n items of data $g(t_j)$ (j=1, 2, ..., n) stored in the built-in memory 52 to a built-in memory of the computer 2.

Absolute values of the data $g(t_j)$ (j=1, 2, ..., n) are summed by the computer 2.

However, the data $g(t_j)$ (j=1, 2, ..., n) does not include waveform data after the bottom echo 16.

When the summed value is smaller than SUM, the summed value is substituted into SUM and the sine wave frequency at that time is substituted into $f_{min}$.

Again, the function generator 3 receives a command from the computer 2 through the GPIB cable 10, and outputs the pulse-shaped sine wave 15 at the sine wave frequency $f_s+\Delta f$ and the timing pulse S at the same time. Then, the same signal processing and calculation are performed.

By increasing the sine wave frequency as $f_s$, $f_s+\Delta f$, $f_s 2\Delta f$, ..., $f_e$ as described above, a frequency $f_{min}$ when the summed value of the data $g(t_j)$ (j=1, 2, ..., n) becomes minimum can be obtained.

When the summed value becomes minimum, the bottom echo 16 in FIG. 19 changes to the bottom echo 16a in FIG. 20.

That is, the obtained $f_{min}$ is the frequency when the ultrasonic wave passes through the gap.

The function generator 3 receives a command from the computer 2 through the GPIB cable 10, and outputs the pulse-shaped sine wave 15 at the sine wave frequency $f_{min}$ and the timing pulse 18.

The pulse-shaped sine wave 15a passes through the gap, and the flaw echo 17 is received by the first sensor 11 and appears in the signal g(t) as shown in FIG. 20.

The computer 2 transfers n items of data $g(t_j)$ (j=1, 2, ..., n) stored in the built-in memory 52 to the built-in memory of the computer 2.

The computer 2 records the data $g(t_j)$ (j=1, 2, ..., n) in the recording medium 5, such as a floppy disk.

The flaw echo 17 is identified from the data $g(t_j)$ (j=1, 2, ..., n).

Figure 22:
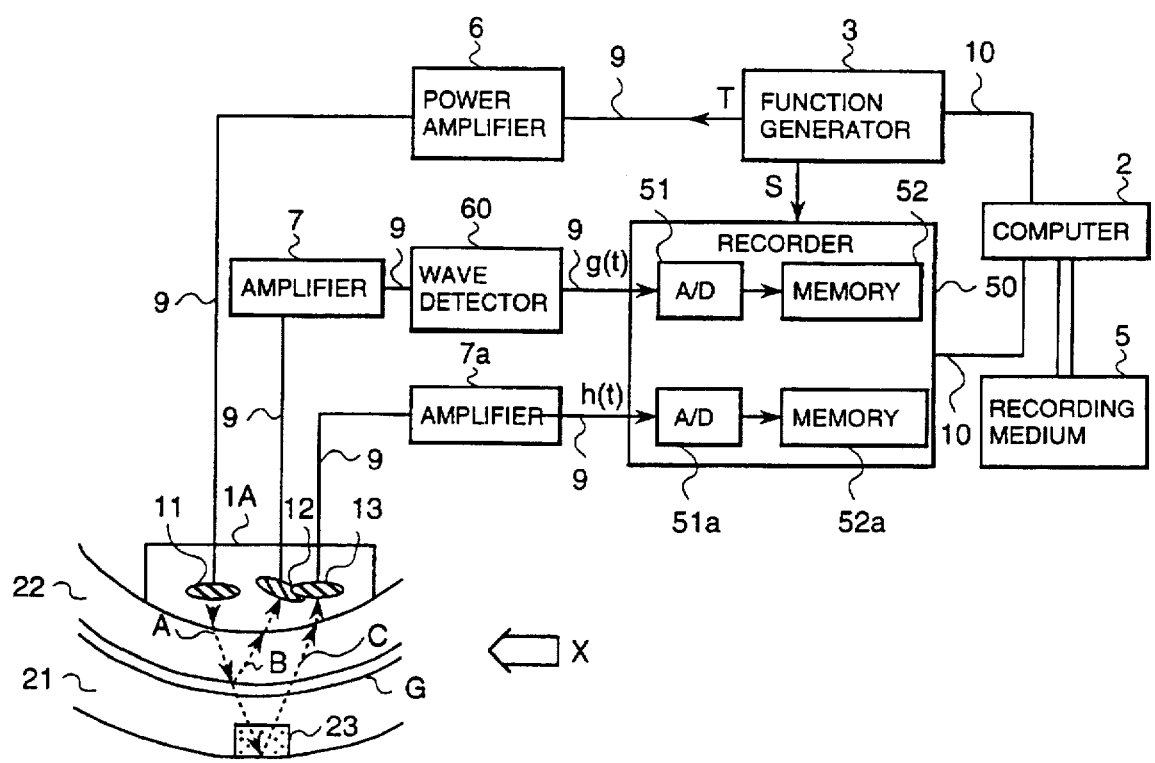
FIG. 22 is a block diagram showing the overall construction of a sixth embodiment of an ultrasonic flaw detecting apparatus in accordance with the present invention.
Figure 23:
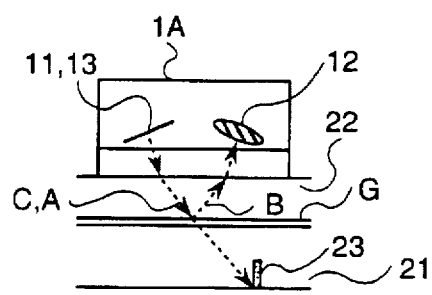
FIG. 23 is a diagram showing the flaw detection as seen in the direction of an arrow X in FIG. 22.

A sixth embodiment according to the present invention is shown in FIG. 22 and FIG. 23.

FIG. 22 is a block diagram showing the sixth embodiment of an ultrasonic flaw detecting apparatus. FIG. 23 is a view seen in the direction of the arrow X in FIG. 22.

The difference between the sixth embodiment and the first embodiment is in the construction of the apparatus. The control algorithm is the same as shown in FIG. 10.

In the sixth embodiment, a wave detector 60 is connected between the amplifier 7 and the recorder 50 in the first embodiment.

Figure 24:
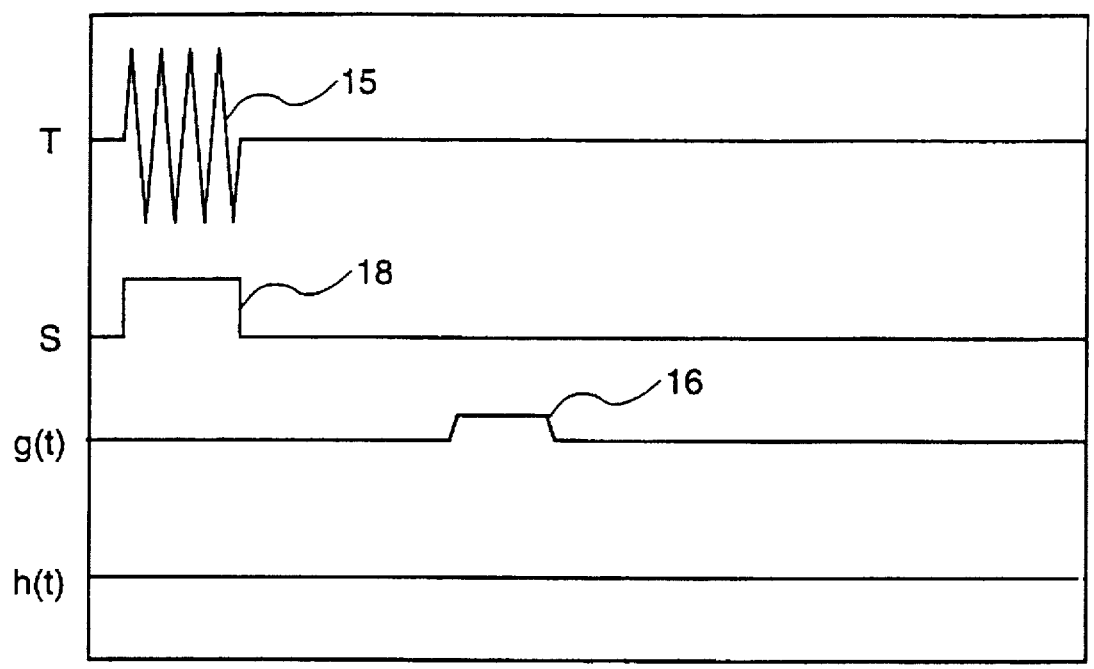
FIG. 24 is a waveform chart of signals T, S, g(t), h(t) in the sixth embodiment where an ultrasonic wave is not transmitted across a gap.
Figure 25:
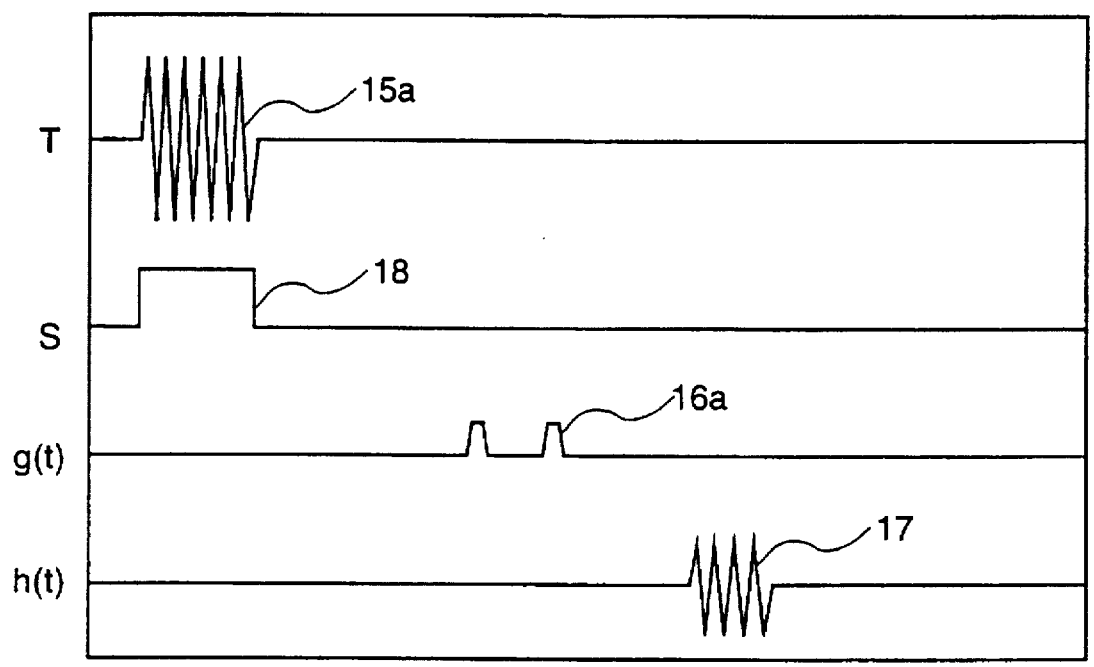
FIG. 25 is a wave form chart of signals T, S, g(t), h(t) in the sixth embodiment where an ultrasonic wave is transmitted across a gap.

By connecting the wave detector in this way, the bottom echoes 16, 16a shown in FIG. 8 and FIG. 9 are changed as shown in FIG. 24 and FIG. 25.

By performing the wave detection of the bottom echo as described above, the value SUM becomes less dependent on the frequency of the pulse-shaped sine wave 15, and accordingly the value $f_{min}$ can be more accurately determined.

Figure 26:
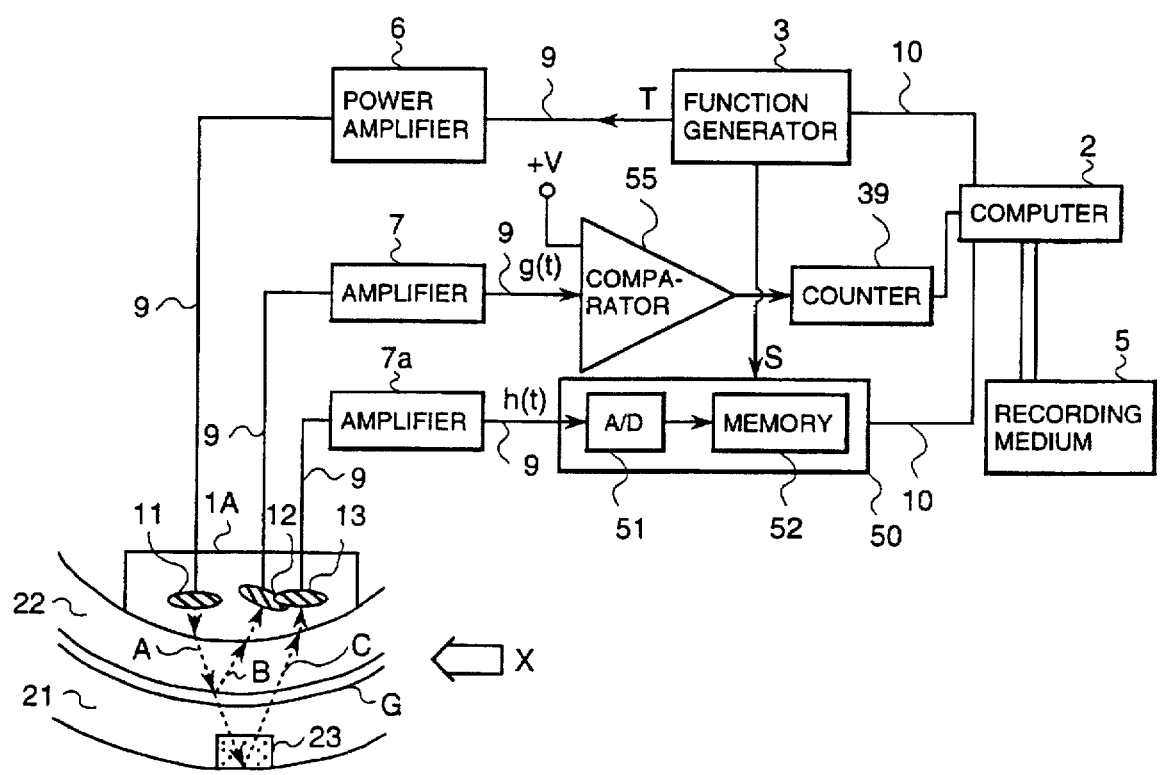
FIG. 26 is a block diagram showing the overall construction of a seventh embodiment of an ultrasonic flaw detecting apparatus in accordance with the present invention.
Figure 27:
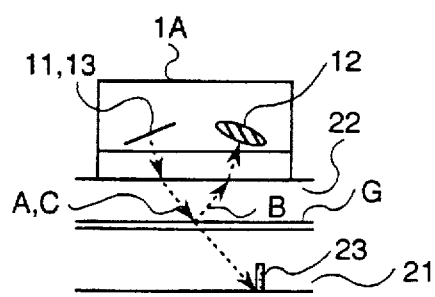
FIG. 27 is a diagram showing the flaw detection as seen in the direction of an arrow X in FIG. 26.

A seventh embodiment according to the present invention is shown in FIG. 26 and FIG. 27.

FIG. 26 is a block diagram showing the seventh embodiment of an ultrasonic flaw detecting apparatus. FIG. 27 is a view seen in the direction of the arrow X in FIG. 26.

Figure 28:
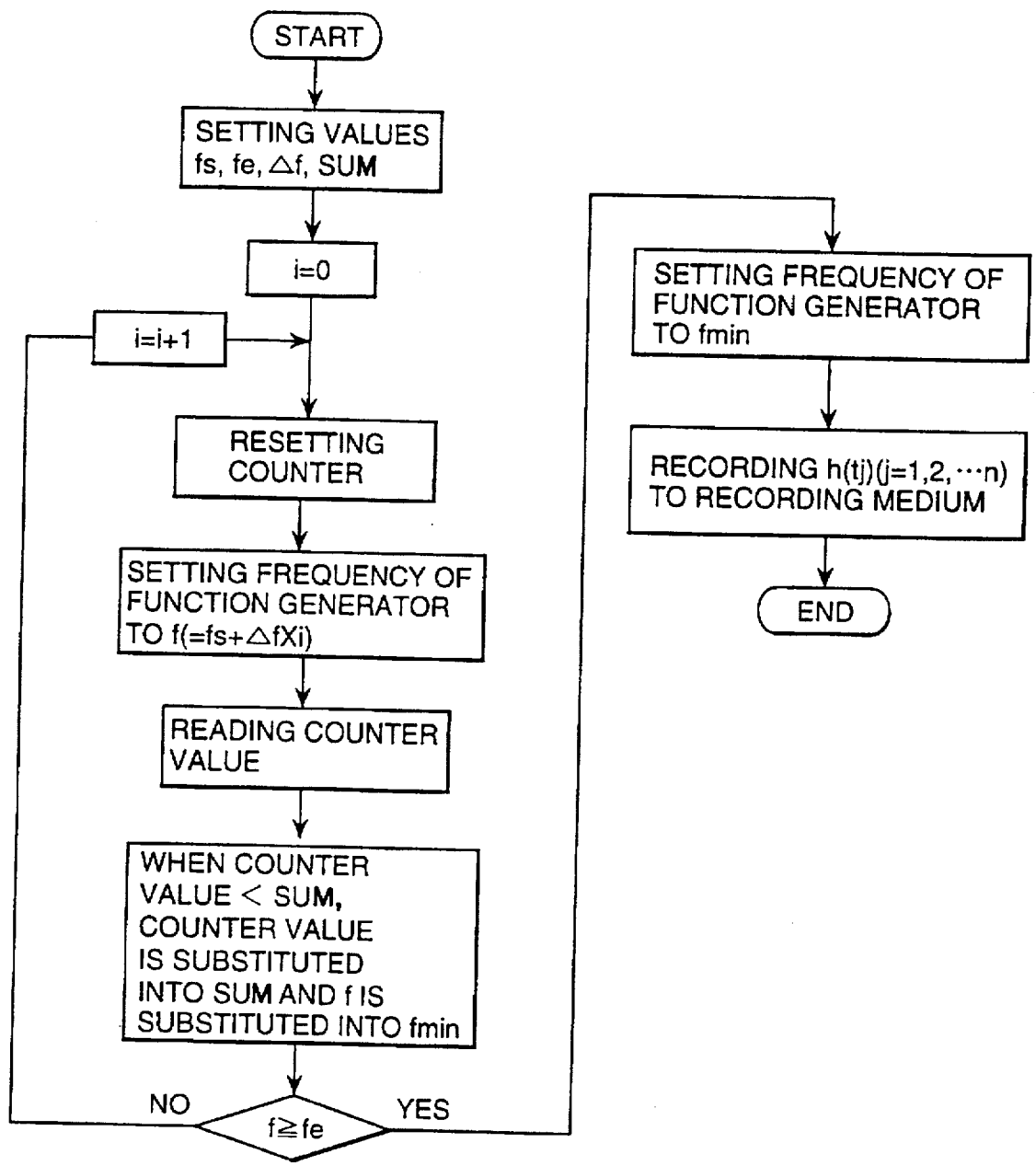
FIG. 28 is a flow chart showing a control algorithm of the seventh embodiment.

The differences between the seventh embodiment and the first embodiment are in the construction of the apparatus and in the control algorithm. The control algorithm is shown in FIG. 28.

The waveforms T, S, g(t), h(t) in the seventh embodiment are the same as those in FIG. 10.

The ultrasonic wave flaw detecting apparatus of the seventh embodiment is composed of a first sensor 11 for launching an ultrasonic wave into the CRD housing 22 along a path A in a slanting direction with respect to the gap G, a function generator 3 for outputting a pulse-shaped sine wave, a power amplifier 6 for amplifying and supplying the pulse-shaped sine wave to the first sensor 11, a second sensor 12 arranged at a position capable of receiving a bottom echo of the CRD housing 22 reflected along a path B, an amplifier 7 for amplifying a received signal of the second sensor 12, a third sensor 13 arranged in a position capable of receiving an echo reflected along a path C from a circumferential direction flaw 23 existing on the bottom surface of the stub-tube 21, that is, in the circumferential direction of the first sensor 11, an amplifier 7a for amplifying a received signal of the third sensor 13, a recorder 50 formed of an A/D converter 51 and a memory 52, a comparator 55 for comparing a voltage V and an output waveform g(t) of the amplifier 7 and generating a voltage of TTL level when the output waveform g(t) is larger than the voltage V, a counter 39 for counting the number of times the voltage of TTL level output from the comparator 55 increases and decreases, a computer 2 for controlling the function generator 3 and the recorder 50 through a GPIB cable 10, and a recording medium 5.

The first sensor 11 and the power amplifier 6, the second sensor 12 and the amplifier 7, the third sensor 13 and the amplifier 7a, the power amplifier 6 and the function generator 3, the amplifier 7 and the comparator 55, the amplifier 7 and the recorder 50, and the comparator 55 and the counter 39, are connected with coaxial cables 9, respectively.

The function generator 3 and the computer 2, and the recorder 50 and the computer 2, are connected with GPIB cable 10, respectively.

A computer 2 having a GPIB interface is used as the computer.

The inspection procedure will be described below, referring to FIG. 28.

Initially, a probe 1A composed of the first, the second and the third sensors is arranged on the inner surface of the CRD housing 22.

Values of $f_s$, fe, $\Delta f$, and SUM in the control program are set by the internal control of the program or by an external input unit, such as a keyboard.

In this embodiment, when the sine wave frequency of the pulse shaped sine wave 15 is scanned from $f_s$ to $f_e$, the pulse width is adjusted so that more than three cycles of sine wave are contained in a pulse.

The value of the counter 39 is reset.

The comparing voltage V of the counter 39 is set to a value smaller than the peak value of the bottom echo 16.

The function generator 3 receives a command from the computer 2 through the GPIB cable 10, and outputs the pulse-shaped sine wave 15 at the sine wave frequency $f_s$ and the timing pulse 18 at the same time. The recorder 50 performs A/D conversion of the signal h(t) using the A/D converter 51 when detecting the leading edge of the timing pulse 18, and records them in a built-in memory 52.

After the pulse-shaped sine wave 15 is amplified using the power amplifier 6, the pulse-shaped sine wave is applied to the first sensor 11 to launch an ultrasonic wave into the CRD housing along the path A.

A bottom echo 16 of the CRD housing 22 is received by the second sensor 12.

The received bottom echo 16 is amplified using the amplifier 7.

The comparator 55 compares the bottom echo 16 with the voltage V. If the bottom echo 16 is larger than the voltage V, the comparator 55 generates the voltage of TTL level.

The counter 39 counts the number of times the voltage of TTL level output from the comparator increases and decreases.

The counter value is transferred to the built-in memory of the computer 2.

When the counter value is smaller than SUM, the counter value is substituted into SUM and the sine wave frequency at that time is substituted into $f_{min}$.

Again, the function generator 3 receives a command from the computer 2 through the GPIB cable 10, and outputs the pulse-shaped sine wave 15 at the sine wave frequency $f_s+\Delta f$ and the timing pulse 18 at the same time. And, the same signal processing and calculation are performed.

By increasing the sine wave frequency as $f_s$, $f_s+\Delta f$, $f_s+2\Delta f$, ..., $f_e$ as described above, a frequency $f_{min}$ when the summed value of the data g($t_j$) (j=1, 2, ..., n) becomes a minimum can be obtained.

When the counter value becomes a minimum, the bottom echo 16 in FIG. 8 changes to the bottom echo 16a in FIG. 9.

That is, the obtained frequency $f_{min}$ is the frequency when the ultrasonic wave passes through the gap.

The function generator 3 receives a command from the computer 2 through the GPIB cable 10, and outputs the pulse-shaped sine wave 15 at the sine wave frequency $f_{min}$ and the timing pulse 18.

The pulse-shaped sine wave 15a passes through the gap, and the flaw echo 17 is received by the third sensor 13 and appears in the signal h(t) as shown in FIG. 9.

The computer 2 transfers n items of data h($t_j$) (j=1, 2, ..., n) stored in the built-in memory 52 to the built-in memory of the computer 2.

The computer 2 records the data h($t_j$) (j=1, 2, ..., n) in the recording medium 5, such as a floppy disk.

The flaw echo 17 is identified from the data h($t_j$) (j=1, 2, ..., n).

Figure 29:
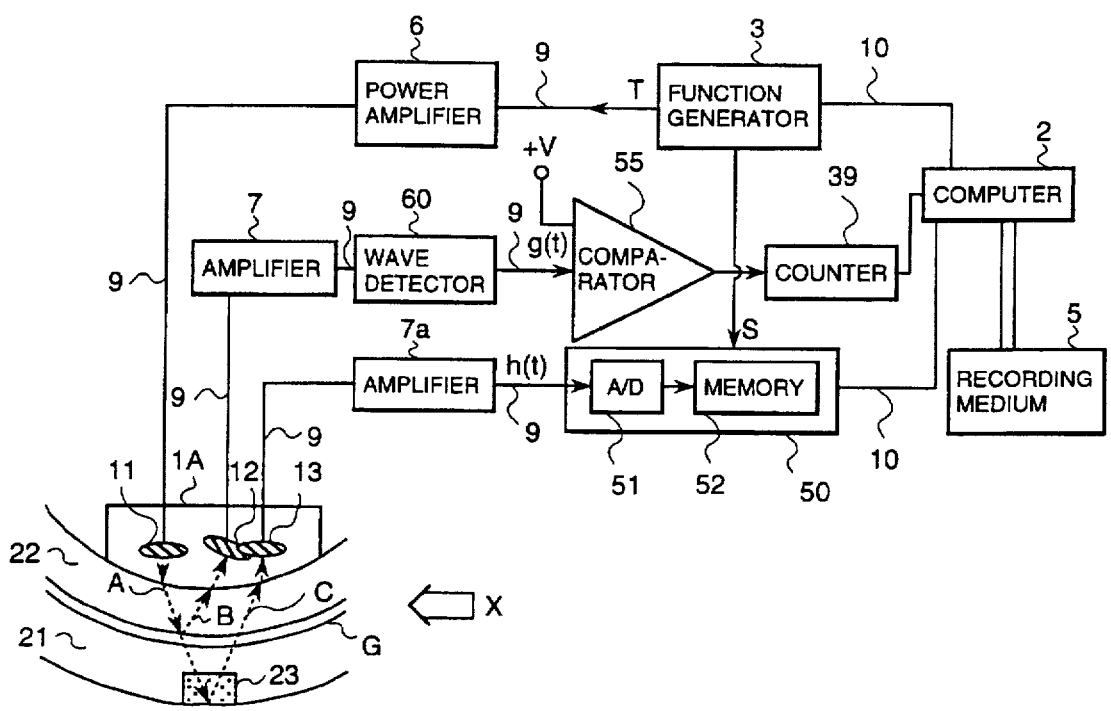
FIG. 29 is a block diagram showing the overall construction of an eighth embodiment of an ultrasonic flaw detecting apparatus in accordance with the present invention.
Figure 30:
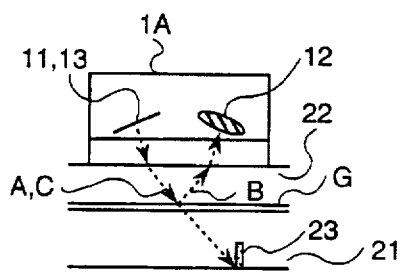
FIG. 30 is a diagram showing the flaw detection as seen in the direction of an arrow X in FIG. 29.

An eighth embodiment according to the present invention is shown in FIG. 29 and FIG. 30.

FIG. 29 is a block diagram showing the eighth embodiment of an ultrasonic flaw detecting apparatus. FIG. 30 is a view seen in the direction of the arrow X in FIG. 29.

The differences between the eighth embodiment and the seventh embodiment are in the construction of the apparatus and in the control algorithm. The signals T, S, g(t), h(t) are the same as those in FIG. 24 and FIG. 25.

Figure 31:
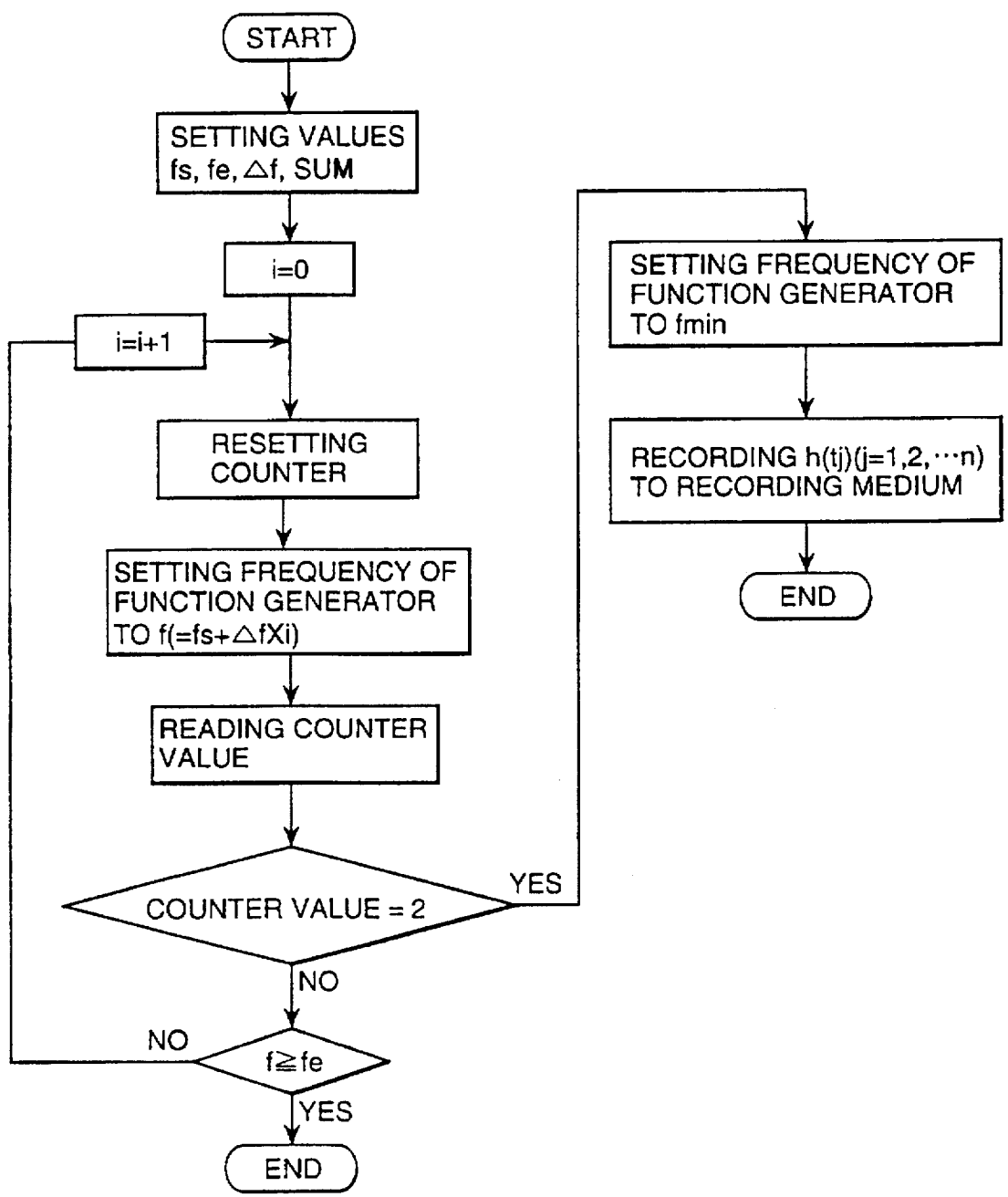
FIG. 31 is a flow chart showing a control algorithm of the eighth embodiment.

The control algorithm is shown in FIG. 31.

In the eighth embodiment, a wave detector 60 is connected between the amplifier 7 and the comparator 55 in the seventh embodiment.

By connecting the wave detector in this way, the bottom echoes 16, 16a shown in FIG. 8 and FIG. 9 are changed as shown in FIG. 24 and FIG. 25.

By using the wave detector as described above, the counter value is not changed depending on the frequency of the pulse-shaped sine wave 15. When the pulse-shaped sine wave 15 does not pass through the gap G, the counter value is 1, and when the pulse-shaped sine wave 15 passes through the gap G, the counter value is 2.

By processing the control algorithm as shown in FIG. 31, waveforms h($t_j$) (j=1, 2, ..., n) containing the flaw echo 17 can be recorded in a recording medium 5.

Figure 32:
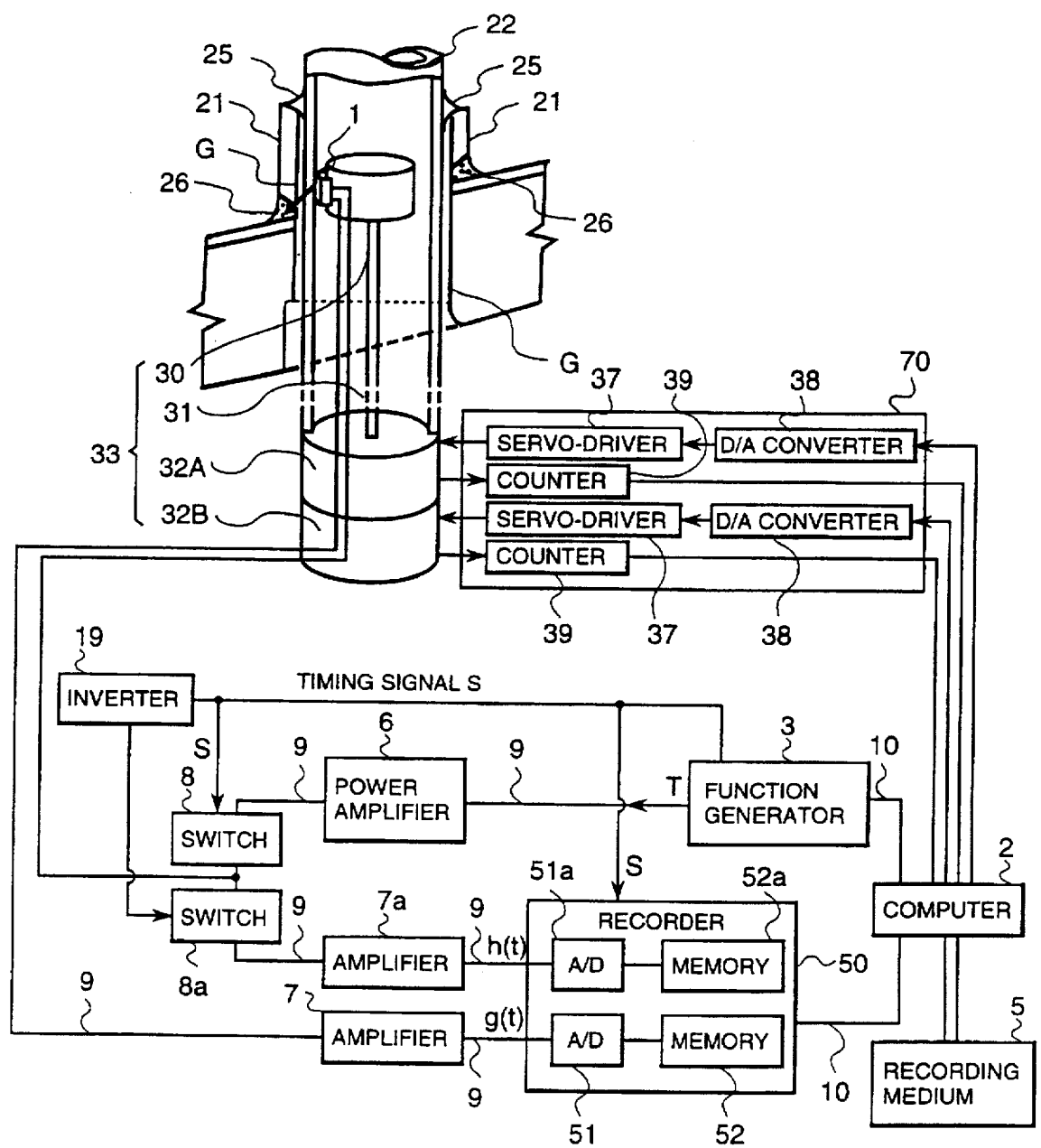
FIG. 32 is a block diagram showing the overall construction of a ninth embodiment of an ultrasonic flaw detecting apparatus in accordance with the present invention.

A ninth embodiment according to the present invention is shown in FIG. 32.

The ultrasonic flaw detecting apparatus of the ninth embodiment is constructed by adding a scanner for the probe 1 in the second or the third embodiment.

The scanner for the probe 1 comprises a probe holder 30, a shaft 31, a scanning mechanism 33 composed of a motor 32A with an encoder for driving in the circumferential direction and a motor 32B with an encoder for driving in the axial direction, a scanning driving mechanism control unit 70 composed of an A/D converter 38, a servo-driver 37 and a counter 39.

The probe 1 is attached to the probe holder 30.

Figure 33:
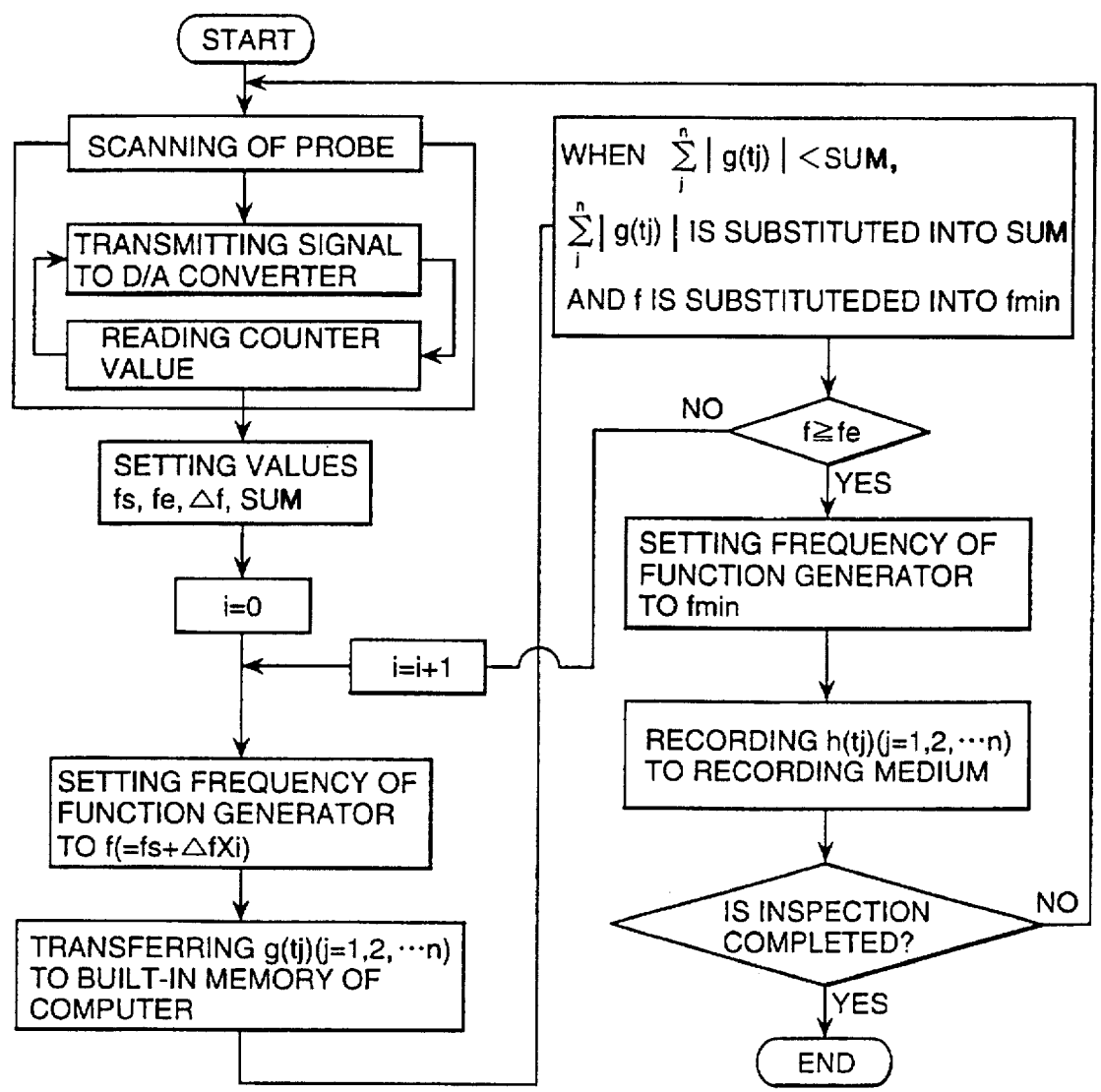
FIG. 33 is a flow chart showing a control algorithm of the ninth embodiment.

FIG. 33 shows a control algorithm indicating how the computer 2 controls the function generator 3, the recorder 50 and the scanning driving mechanism control unit 70 and what calculation the computer performs.

The inspection procedure will be described below.

A command is transmitted from the computer 2 to the scanning driving mechanism control unit 70 to scan the probe 1 to an inspection position using the scanning mechanism 33.

The data $h(t_j)$ is recorded in a recording medium 5 using the same algorithm as in the first embodiment.

The probe 1 scans another inspection portion and the data $h(t_j)$ is recorded in a recording medium 5 in the same manner as indicated above.

By scanning the probe 1 inside the CRD housing 22, all positions of the stub-tube can be inspected.

The scanning mechanism 33 may be provided with a mechanism capable of travelling inside the tube. In a case where the probes 1A and 1B are mounted on the probe holder 30, the switch 8 is not needed.

Further, in a case where the probes 1A and 1B, and the probes 1C and 1D are combined and mounted on the scanning drive mechanism 33, both a circumferential direction flaw and an axial direction flaw can be detected.

Figure 34:
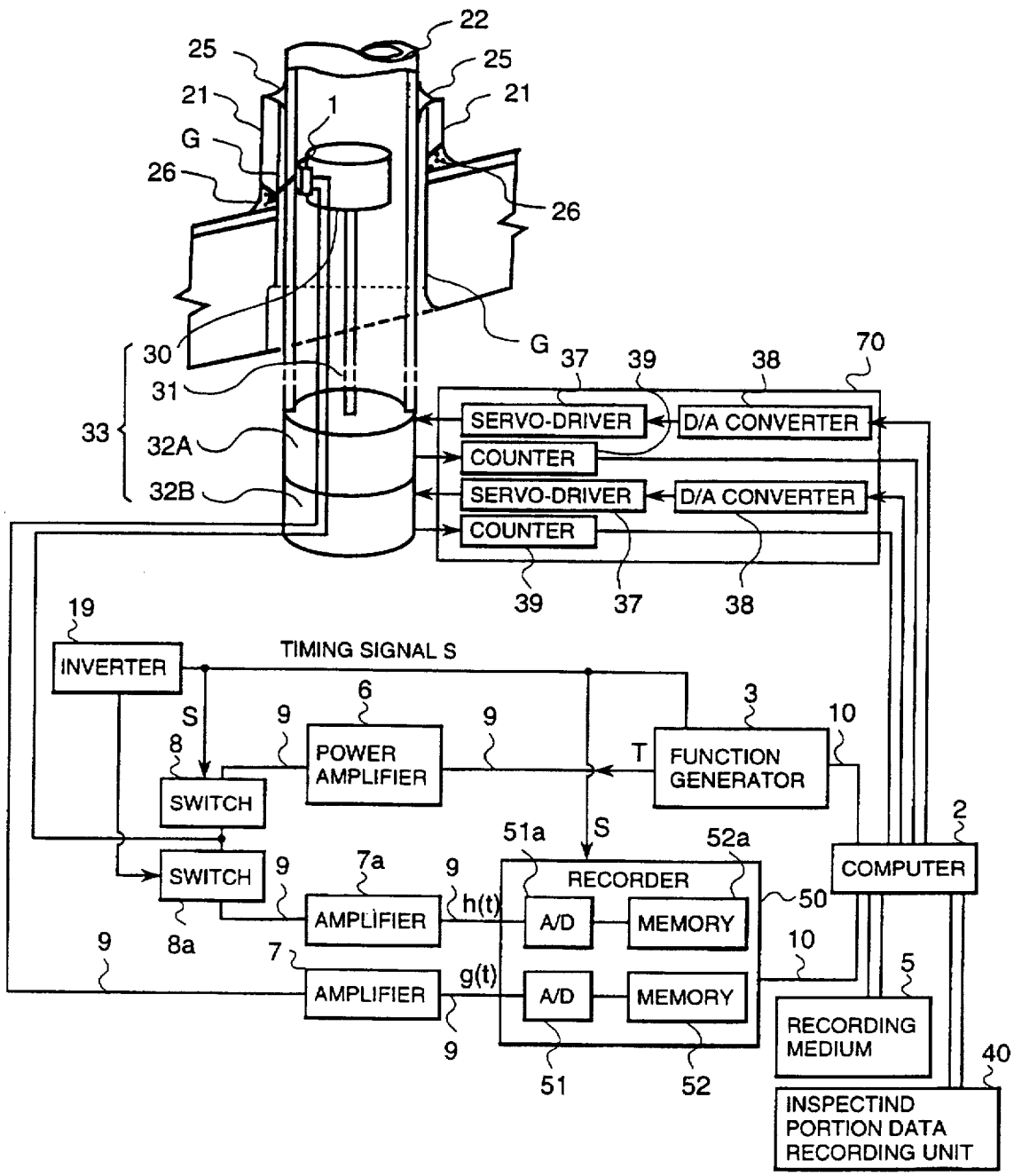
FIG. 34 is a block diagram showing the overall construction of a tenth embodiment of an ultrasonic flaw detecting apparatus in accordance with the present invention.
Figure 35:
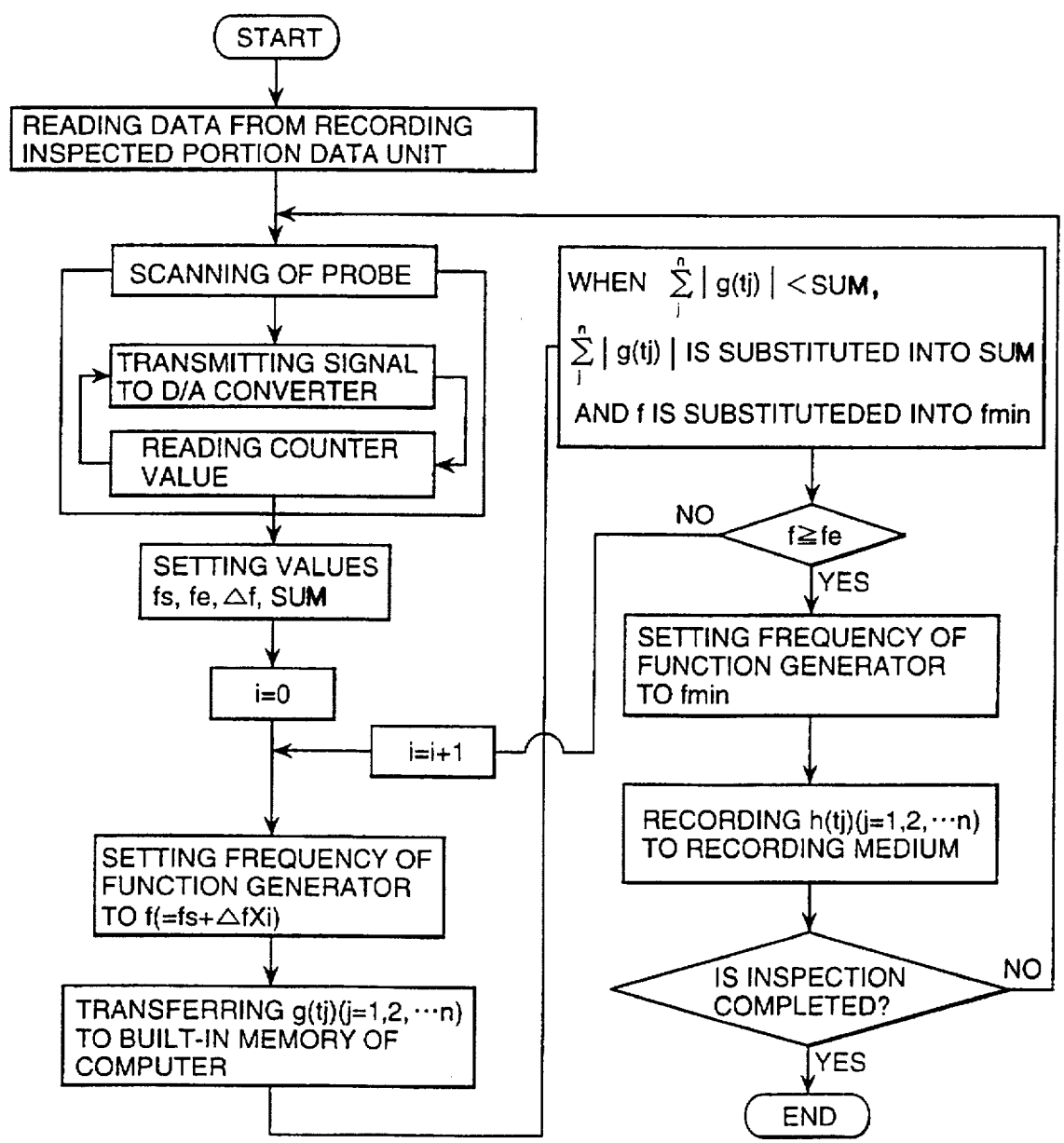
FIG. 35 is a flow chart showing a control algorithm of the tenth embodiment.

FIG. 34 shows a tenth embodiment in accordance with the present invention.

The tenth embodiment is an ultrasonic flaw detecting apparatus which is formed by adding an inspected portion data recording unit 40 to the ninth embodiment.

A flaw in a stub-tube 21 often occurs in a heat affected zone near a welded portion 25 or 26, as shown in FIG. 34.

Therefore, it is possible to efficiently inspect the stub-tube 21 by scanning the probe 1 along weld lines of the welded portions 25, 26.

However, the shape of the welded portion differs depending on the portion of the pressure vessel 20 in which the stub-tube 21 is arranged.

Therefore, by storing data concerning positions and shapes of welded portions for all of the stub-tubes 21 welded to the pressure vessel 20 in the inspected portion data recording unit 40 and by scanning the probe 1 along the weld lines of the welded portions 26 based on the data, it is possible to inspect the stub-tubes 21 efficiently.

Figure 36:
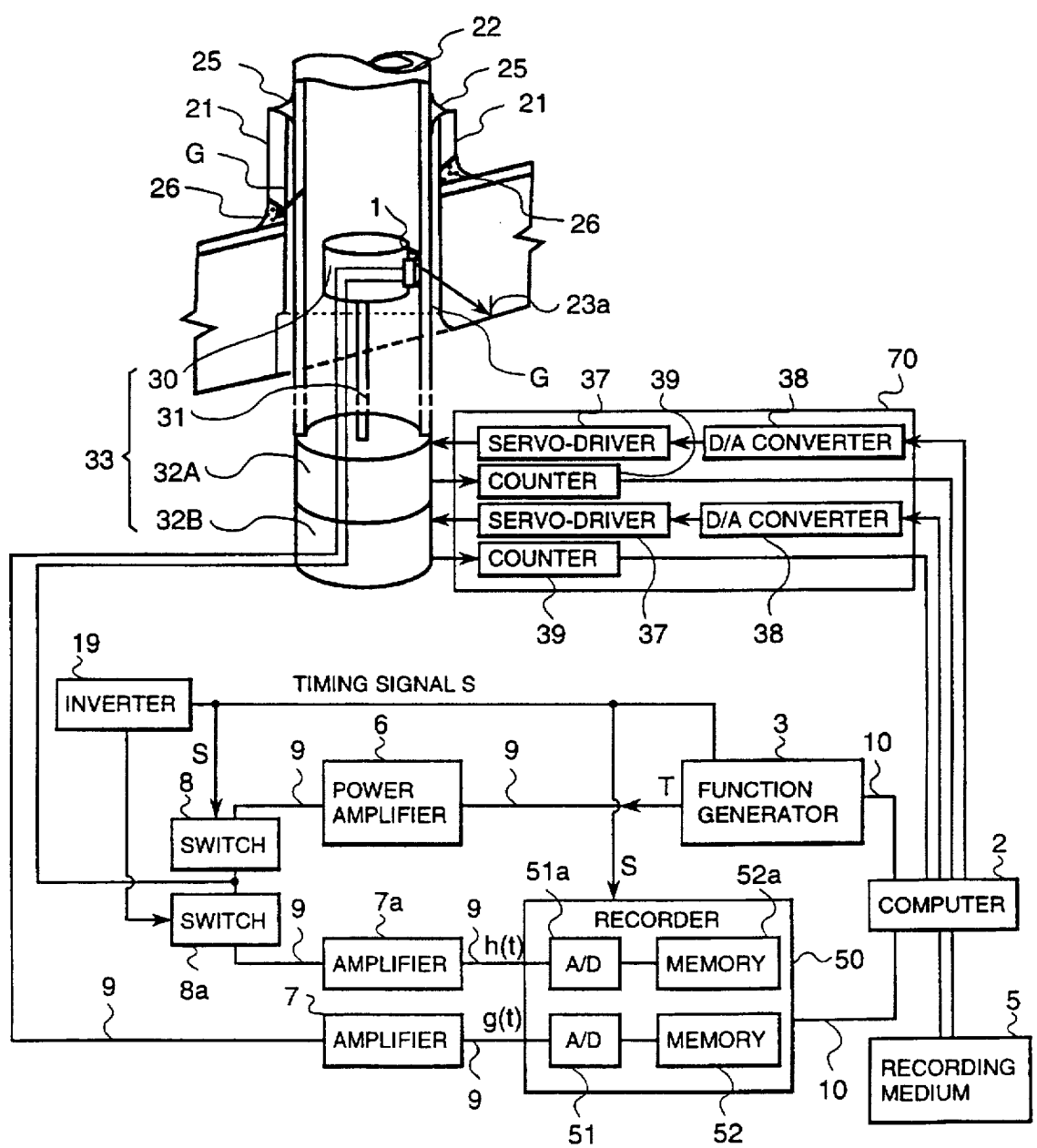
FIG. 36 is a block diagram showing the overall construction of an eleventh embodiment of an ultrasonic flaw detecting apparatus in accordance with the present invention.

FIG. 36 shows an eleventh embodiment in accordance with the present invention.

The first embodiment to the tenth embodiment are concerned with how to perform inspection of the stub-tube 21. However, it is also possible to detect a flaw in the bottom head of the pressure vessel 20 by arranging the probes 1C, 1D and 1E at the positions shown in FIG. 36.

Since the other features of this embodiment are the same as in the ninth embodiment, the description thereof will be omitted here.

The medium inside the gap used in the aforementioned embodiments will be described below.

Although the medium inside the gap G of FIG. 4 is commonly air, transmission frequencies of the gap are calculated using Equation 3 and the results are shown in Table 1 for cases where the medium inside the gap is air, helium or water.

Therein, sound velocities in air, helium and water are assumed to be 340, 1000 and 1480 m/s, respectively.

TABLE 1

| PROPAGATION LENGTH IN GAP (mm) | TRANSMISSION FREQUENCY (MHz) | | | | | |
|---|---|---|---|---|---|---|
| | n = 0 | | | n = 1 | | |
| | AIR | HELIUM | WATER | AIR | HELIUM | WATER |
| 0.1 | 1.7 | 5 | 7.4 | 3.4 | 10 | 14.8 |
| 0.12 | 1.42 | 4.17 | 6.17 | 2.83 | 8.33 | 12.3 |
| 0.14 | 1.21 | 3.57 | 5.29 | 2.43 | 7.14 | 10.57 |
| 0.16 | 1.06 | 3.13 | 4.63 | 2.13 | 6.25 | 9.25 |
| 0.18 | 0.94 | 2.78 | 4.11 | 1.89 | 5.56 | 8.22 |
| 0.2 | 0.85 | 2.5 | 3.7 | 1.7 | 5 | 7.4 |
| 0.22 | 0.77 | 2.27 | 3.36 | 1.55 | 4.54 | 6.73 |

Figure 37:
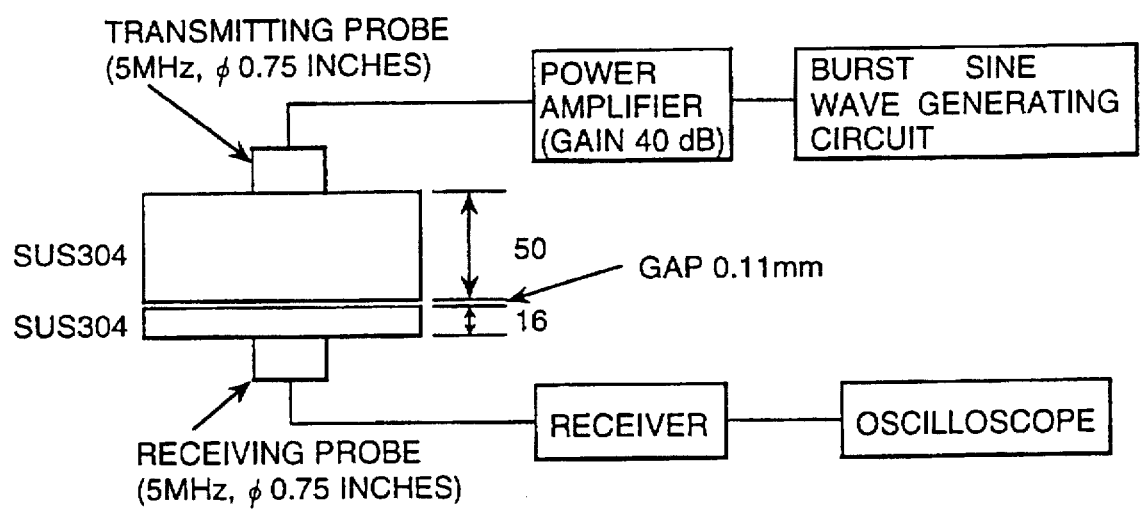
FIG. 37 is a schematic diagram of an experimental apparatus by which data for the embodiments of the present invention has been obtained.

Table 2 shows measured results of transmission coefficients using an experimental apparatus of FIG. 37 for cases where the medium inside the gap is air, helium or water. Therein, the gap width is set to 0.11 mm.

TABLE 2

| MEDIUM | TRANSMISSION FREQUENCY (MHz) | TRANSMISSION COEFFICIENT (dB) |
|---|---|---|
| AIR | 6.59 | −70 |
| HELIUM | 4.38 | −70 |
| WATER | 4.32 | −5 |

It can be understood from Table 2 that, in a case where the medium in the gap is a gas, the transmission coefficient of the ultrasonic wave is small and the round-trip ultrasonic wave in the gap is attenuated by −140 dB, and accordingly it is difficult to detect an echo reflected from a flaw existing at a place beyond the gap.

Therefore, it is necessary to use a liquid, such as water, alcohol, glycerin, oil and the like, or a solid, as the medium inside the gap.

In a case of filling the inside of the gap with a liquid, the gap can be easily filled with the liquid by sucking air inside the gap to bring the gap nearly to a vacuum state.

According to the first aspect of the present invention, an ultrasonic wave can be transmitted into and received from a deep portion of a multi-layer structure having different acoustic impedances, and consequently there is an effect that a flaw existing in a deep portion of the multi-layer structure can be certainly detected.

According to the second aspect of the present invention, an ultrasonic wave can be efficiently transmitted into and received from a deep portion of a multi-layer structure having different acoustic impedances using a plurality of ultrasonic sensors, and consequently there is an effect that a flaw existing in a deep portion of the multi-layer structure can be certainly detected.

According to the third aspect of the present invention, an ultrasonic wave can be transmitted into and received from a deep portion of a multi-layer structure having different acoustic impedances using a small number of sensors by switching a plurality of the ultrasonic sensors, and consequently there is an effect that a flaw existing in a deep portion of the multi-layer structure can be certainly detected.

According to the fourth aspect of the present invention, there is an effect that an ultrasonic wave can be efficiently transmitted into and received from a deep portion of a multi-layer structure having different acoustic impedances using a single sensor.

According to the fifth aspect of the present invention, in addition to any one of the effects from the first aspect to the fourth aspect, there is an effect that the ultrasonic wave energy transmitted in a round-trip across the middle layer can be increased.

According to the sixth aspect of the present invention, in addition to any one of the effects from the first aspect to the fourth aspect, there is an effect that an ultrasonic wave can be transmitted and received easily since all the sensors can be handled at one time.

According to the seventh aspect of the present invention, in addition to any one of the effects from the first aspect to the fourth aspect, there is an effect that energy of an ultrasonic wave can be suppressed so as to be attenuated as much as possible by employing a liquid having a large transmission coefficient for an ultrasonic wave as the medium.

According to the eighth aspect of the present invention, there is an effect that the effect of any one of the first aspect to the fourth aspect can be easily attained by employing water.

According to the ninth aspect of the present invention, there is an effect that it is possible to easily set the frequency of an ultrasonic wave in which the ultrasonic wave can be efficiently transmitted into and received from a deep position of a multi-layer structure having different acoustic impedances.

According to the tenth aspect of the present invention, there is an effect that it is possible to easily set the frequency of an ultrasonic wave in which the ultrasonic wave can be efficiently transmitted into and received from a deep position of a multi-layer structure having different acoustic impedances, and consequently there is an effect that a flaw existing in a deep portion of the multi-layer structure can be certainly detected.

What is claimed is:

1. An ultrasonic flaw detecting apparatus for inspecting a multi-layer structure, which apparatus comprises:

ultrasonic wave transmitting means acoustically connected to a multi-layer structure composed of not less than three layers including a middle layer, the middle layer being formed of a medium having an acoustic impedance different from the adjacent layers on either side thereof;

first ultrasonic wave receiving means acoustically connected to said multi-layer structure at a position for receiving a boundary echo from an interface of a first layer adjacent to said middle layer, the first layer existing on the transmitting means side of said middle layer;

second ultrasonic wave receiving means acoustically connected to said multi-layer structure at a position for receiving an echo from the inside of a second layer existing on the other side of said middle layer from the transmitting means;

a function generator for outputting and supplying a pulse-shaped sine wave to said transmitting means;

frequency control means for varying the sine wave frequency of the pulse-shaped sine wave output from said function generator;

intensity detecting means for detecting the intensity of a signal based on an output of said first ultrasonic wave receiving means for receiving the boundary echo; and means for indicating the intensity of a signal based on an output of said second ultrasonic wave receiving means for receiving the echo from the inside of the second layer.

2. An ultrasonic flaw detecting apparatus for inspecting a multi-layer structure, which apparatus comprises:

a first sensor arranged so as to transmit an ultrasonic wave in a slanting direction with respect to a multi-layer structure composed of not less than three layers, including a middle layer, the middle layer being formed of a medium having an acoustic impedance different from the adjacent layers on either side thereof;

a function generator for outputting and supplying a pulse-shaped sine wave to said first sensor;

a power amplifier for amplifying the pulse-shaped sine wave output from said function generator;

frequency control means for varying the sine wave frequency of the pulse-shaped sine wave output from said function generator;

a second sensor arranged so as to receive a boundary echo of an interface of a first layer adjacent to said middle layer, the first layer existing on the first sensor side of said middle layer;

a first amplifier for amplifying a signal of the boundary echo received by said second sensor;

intensity detecting means for detecting the intensity of a signal based on an output of said first amplifier;

a third sensor arranged so as to receive an echo from the inside of a second layer existing on the other side of said middle layer from said first sensor;

a second amplifier for amplifying a signal of the echo received by said third sensor; and means for indicating a signal based on an output of said second amplifier.

3. An ultrasonic flaw detecting apparatus for inspecting a multi-layer structure, which apparatus comprises:

a first sensor arranged so as to transmit an ultrasonic wave in a slanting direction with respect to a multi-layer structure composed of not less than three layers, including a middle layer, the middle layer being formed of a medium having an acoustic impedance different from the adjacent layers on either side thereof, and to receive an echo from the inside of a second layer existing on the other side of said middle layer from the transmitting side;

a function generator for outputting and supplying a pulse-shaped sine wave to said first sensor;

a power amplifier for amplifying the pulse-shaped sine wave output from said function generator;

frequency control means for varying the sine wave frequency of the pulse-shaped sine wave output from said function generator;

a second amplifier for amplifying a signal of an echo received by said first sensor;

switching means for selectively connecting said power amplifier and said second amplifier to said first sensor;

a second sensor arranged so as to receive a boundary echo of an interface of a first layer adjacent to said middle layer, the first layer existing on the first sensor side of said middle layer;

a first amplifier for amplifying a signal of the boundary echo received by said second sensor;

intensity detecting means for detecting the intensity of a signal based on an output of said first amplifier; and means for indicating a signal based on an output of said second amplifier.

4. An ultrasonic flaw detecting apparatus for inspecting a multi-layer structure, which apparatus comprises:

a first sensor arranged so as to transmit an ultrasonic wave to a multi-layer structure composed of not less than three layers, including a middle layer, in a thickness direction normal to the multi-layer structure, the middle layer being formed of a medium having an acoustic impedance different from the adjacent layers on either side thereof, and to receive an echo from the inside of a second layer existing on the other side of said middle layer from the transmitting side;

a function generator for outputting and supplying a pulse-shaped sine wave to said first sensor;

a power amplifier for amplifying the pulse-shaped sine wave output from said function generator;

frequency control means for varying the sine wave frequency of the pulse-shaped sine wave output from said function generator;

a first amplifier for amplifying a signal of a boundary echo received by said first sensor;

intensity detecting means for detecting the intensity of a signal based on an output of said first amplifier;

a second amplifier for amplifying a signal of an echo other than the boundary echo received by said first sensor;

switching means for selectively connecting said power amplifier, said first amplifier, and said second amplifier to said first sensor; and means for indicating a signal based on an output of said second amplifier.

5. An ultrasonic flaw detecting apparatus for inspecting a multi-layer structure according to any one of claim 1 to claim 4, wherein said function generator outputs a pulse wave having at least two components of sine wave frequencies expressed by a ratio of integers to each other.

6. An ultrasonic flaw detecting apparatus for inspecting a multi-layer structure according to any one of claim 1 to claim 4, wherein all of said sensors are mounted in a single probe shoe.

7. An ultrasonic flaw detecting apparatus for inspecting a multi-layer structure according to any one of claim 1 to claim 4, wherein said medium is a liquid.

8. An ultrasonic flaw detecting apparatus for inspecting a multi-layer structure according to any one of claim 1 to claim 4, wherein said medium is water.

9. An ultrasonic flaw detecting apparatus for inspecting a multi-layer structure according to any one of claim 1 to claim 4, which further comprises judging means for judging a sine wave frequency of said intensity detecting means at the time of detecting the lowest intensity; and control means for receiving a judged result from said judging means and adjusting the output frequency of said function generator to said sine wave frequency at the time of detecting said lowest intensity.

10. An ultrasonic flaw detecting method, comprising the steps of:

transmitting an ultrasonic wave to a multi-layer structure, in which a middle layer is disposed between a first layer and a second layer from said first layer while the frequency of the ultrasonic wave is varied, the middle layer having an acoustic impedance different from the acoustic impedances of both of the first and the second layers;

receiving a boundary echo from the interface between said first layer and said middle layer every time said frequency is varied;

detecting a received intensity of said boundary echo;

receiving an echo from the inside of said second layer as an inspected result, when an ultrasonic wave having a frequency, at which the lowest level of received intensity is produced, is transmitted to the multi-layer structure; and displaying said inspected result.

* * * * *